(12) United States Patent
Nelson et al.

(10) Patent No.: US 10,323,011 B2
(45) Date of Patent: Jun. 18, 2019

(54) PKC-ACTIVATING COMPOUNDS FOR THE TREATMENT OF NEURODEGENERATIVE DISEASES

(71) Applicant: Cognitive Research Enterprises, Inc., Morgantown, WV (US)

(72) Inventors: Thomas J. Nelson, Morgantown, WV (US); Daniel L. Alkon, Chevy Chase, MD (US)

(73) Assignee: COGNITIVE RESEARCH ENTERPRISES, INC., Morgantown, WV (US)

( * ) Notice: Subject to any disclaimer, the term of this patent is extended or adjusted under 35 U.S.C. 154(b) by 0 days.

(21) Appl. No.: 14/803,762

(22) Filed: Jul. 20, 2015

(65) Prior Publication Data

US 2016/0060236 A1    Mar. 3, 2016

Related U.S. Application Data

(60) Division of application No. 13/401,459, filed on Feb. 21, 2012, now Pat. No. 9,119,825, which is a continuation of application No. 12/510,681, filed on Jul. 28, 2009, now Pat. No. 8,163,800.

(60) Provisional application No. 61/084,172, filed on Jul. 28, 2008.

(51) Int. Cl.
| | |
|---|---|
| *C12N 9/12* | (2006.01) |
| *A61K 31/23* | (2006.01) |
| *A61P 25/00* | (2006.01) |
| *A61P 25/28* | (2006.01) |
| *A61K 31/201* | (2006.01) |
| *A61K 31/231* | (2006.01) |
| *C07C 53/134* | (2006.01) |
| *C07C 69/608* | (2006.01) |
| *C07C 31/13* | (2006.01) |
| *A61K 31/045* | (2006.01) |
| *A61K 31/335* | (2006.01) |
| *C07C 31/133* | (2006.01) |
| *C07D 303/40* | (2006.01) |
| *C07D 303/42* | (2006.01) |

(52) U.S. Cl.
CPC .......... *C07D 303/42* (2013.01); *A61K 31/045* (2013.01); *A61K 31/201* (2013.01); *A61K 31/23* (2013.01); *A61K 31/231* (2013.01); *A61K 31/335* (2013.01); *A61P 25/00* (2018.01); *A61P 25/28* (2018.01); *C07C 31/13* (2013.01); *C07C 31/1333* (2013.01); *C07C 53/134* (2013.01); *C07C 69/608* (2013.01); *C07D 303/40* (2013.01); *C12N 9/12* (2013.01); *C12Y 207/11013* (2013.01)

(58) Field of Classification Search
CPC .... A61K 31/045; A61K 31/201; A61K 31/23; A61K 31/231; A61K 31/335; C07C 31/13; C07C 31/1333; C07C 53/134; C07C 69/608; C07D 303/40; C07D 303/42; C12N 9/12; C12Y 207/11013
See application file for complete search history.

(56) References Cited

U.S. PATENT DOCUMENTS

| | | | |
|---|---|---|---|
| 5,242,932 | A | 9/1993 | Gandy et al. |
| 5,385,915 | A | 1/1995 | Buxbaum et al. |
| 6,077,686 | A | 6/2000 | Der et al. |
| 6,080,582 | A | 6/2000 | Alkon et al. |
| 6,080,784 | A | 6/2000 | Driedger et al. |
| 6,107,050 | A | 8/2000 | Alkon et al. |
| 7,468,389 | B2 * | 12/2008 | Nishizaki .............. C07C 53/134 514/531 |
| 7,595,167 | B2 | 9/2009 | Khan et al. |
| 2001/0051344 | A1 | 12/2001 | Shalon et al. |
| 2003/0108956 | A1 | 6/2003 | Alkon et al. |
| 2003/0153014 | A1 | 8/2003 | Shen et al. |
| 2004/0014678 | A1 | 1/2004 | Favit et al. |
| 2004/0086905 | A1 | 5/2004 | Das et al. |
| 2005/0059092 | A1 | 3/2005 | Zhao et al. |
| 2005/0075393 | A1 | 4/2005 | Tomoyuki |
| 2007/0082366 | A1 | 4/2007 | Khan et al. |
| 2009/0029873 | A1 | 1/2009 | Khan et al. |

FOREIGN PATENT DOCUMENTS

| | | |
|---|---|---|
| EP | 0 735 370 A | 10/1996 |
| JP | 06-279311 | 10/1994 |
| JP | 10-090263 A | 4/1998 |
| WO | WO 93/11231 A | 6/1993 |

(Continued)

OTHER PUBLICATIONS

Beaumont et al., "Design of ester prodrugs to enhance oral absorption of poorly permeable compounds: challenges to the discovery scientist," Curr. Drug Metabol. 2003l 4(6): 461-85; abstract only.*

(Continued)

*Primary Examiner* — Sreenivasan Padmanabhan
*Assistant Examiner* — Jody L Karol
(74) *Attorney, Agent, or Firm* — Scully, Scott, Murphy & Presser, P.C.

(57) ABSTRACT

The present invention relates to methods of activate an isoform of protein kinase C (PKC) for the treatment of neurological diseases including Alzheimer's disease and stroke using cyclopropanated or epoxidized derivatives of mono- and polyunsaturated fatty acids. The present invention also relates to methods of reducing neurodegeneration using cyclopropanated or epoxidized derivatives of mono- and polyunsaturated fatty acids.

3 Claims, 12 Drawing Sheets

(56) References Cited

FOREIGN PATENT DOCUMENTS

| WO | WO 2000/20867 A | 4/2000 |
|---|---|---|
| WO | WO 2000/70099 | 11/2000 |
| WO | WO 2001/69244 A2 | 9/2001 |
| WO | WO 2002/10768 A2 | 2/2002 |
| WO | WO 2002/50013 A1 | 6/2002 |
| WO | WO 2002/067764 | 9/2002 |
| WO | WO 2003/102016 A2 | 12/2003 |
| WO | WO 2004/083241 A2 | 9/2004 |
| WO | WO 2006/050475 | 5/2006 |
| WO | WO 2006/054979 A1 | 5/2006 |
| WO | WO 2007/043998 | 4/2007 |
| WO | WO 2007/044094 A1 | 4/2007 |
| WO | WO 2007/047029 | 4/2007 |
| WO | WO 2007/149985 A2 | 12/2007 |
| WO | WO 2008/100449 | 8/2008 |
| WO | WO 2008/148115 A1 | 12/2008 |

OTHER PUBLICATIONS

Adachi, M., et al., "Two Co-existing Mechanisms for Nuclear Import of MAP Kinase: Passive Diffusion of a Monomer and Active Transport of a Dimer", EMBO J., 18, 5347-5358 (1999).

Alessi, D.R, "Inactivation of p42 MAP Kinase by Protein Phosphatase 2A and a Protein Tyroin Phosphatase, but not CL100, in Various Cell Lines", Current Biol. 5, 283-295 (1995).

Alkon et al., Protein Synthesis Required for Long-Term Memory is Induced by PKC Activation on Days Before Associative Learning, Proc. Natl. Acad. Sci. USA,102:16432-16437 (2005).

Anderson et al., "Oxidative Signalling and Inflammatory Pathways in Alzheimer's Disease," Biochem. Soc. Symp., 67:141-149 (2001).

Arendt et al.,"Increased Expression and Subcellular Translocation of the Mitogen Activated Protein Kinase Kinase and Mitogen-Activated Protein Kinase in Alzheimer's Disease," Neuroscience, 68(1):5-18 (1995).

Bailn et al., "Normal replicative lifespan of Alzheimer skin fibroblasts", Neurobiol Aging, vol. 9, pp. 195-198 (1988).

Baker et al., "System Manifestation of Alzheimer's Disease," Age, 11:60-65 (1988).

Barrow et al., "Functional Phenotype in Transgenic Mice Expressing Mutant Human Presenilin-1," Nuerogiology of Disease 7, 119-126 (2000).

Bassa BV, et al.,."Lysophosphatidylcholine Activates Mesangial Cell PKKC and MAP Kinase by PLCy-1and Tyrosine Kinase-Ras Pathways," Am J Physiol, 277:F328-2337 (1999).

Becton, Dickenson& Co., BD GentestTM Primary Hepatocytes, 13 (2008).

Bernier et al., "Bradykinin-regulated Interactions of the Mitogen-activated Protein Kinase Pathway with the Endothelial Nitric-oxide Synthase," J. Biol. Chem., 275:30707-30715 (2000).

Berridge, "Inositol Triphosphate and Diacylglycerol as Second Messengers," Biochem J., 220:345-360 (1984).

Biernat et al., "Phosphorylation of Ser 262 Strongly Reduces Binding of Tau to Microtubules: Distinction beteen PHF-like Immunoreactivity and Microtubule Binding," Neuron, 11:153-163 (1993).

Billingsley, M.L. et al.,." Regulated Phosphorylation and Dephosphorylation of tau Protein: Effects on Microtubule Interaction, Intracellular Trafficking and Neurodegeneration", Biochem. J. 323,557-591 (1997).

Blanchard et al., "Hyperphosphorylation of Human TAU by Brain Kinase PK40et beyond Phosphorylation 12 by cAMP-dependent PKA: Relation to Alzheimer's Disease." Biochem. Biophys. Res. Commun., 200(1):187-194 (1994).

Blobe et al.,"Regulation of protein kinase C and role in cancer biology,"Cancer Metast. Rev. 1994; 13:411-431.

Bockman et al., "Kinins and Kinin Receptors: Importance for the Activation of Leukocytes," Journal of Leukocyte Biology, 68 (Nov. 2000).

Bondy et al., "The PHA-Induced Calcium Signal in Lymphocytes is Altered After Blockade of K+-Channels in Alzheimer's Disease," J. Psychiat. Res., 30(3):217-227 (1996).

Braconi Quintaje, S:B. et al., "Role of Protein Phosphatase 2a in the Regulation of Mitogenactivated Protein Kinase Activity in Ventricular Cardiomyocytes", Biochem. Biophys. Res. Commun. 221, 539-547 (1996).

Brooks et al., "Gene Expression Profiles of Metabolic Enzyme Transcripts in Alzheimer's Disease," Brain Res, 1127(1):127-135 (2007).

Brunet, A., "Nuclear translocation of p42/p44 Mitogen-activated Protein Kinase is Required for Growth Factor-induced Gene Expression and Cell Cycle Entry", EMBO J. 18,664-674 (1999).

Burke et al., "Update on Alzheimer's Disease: Promising advances in Detection and Treatment," Postgraduate Medicine, 106(5) (1999).

Bush, et al., Pharmacol Ther., 56:97-117 (1992).

Buxbaum et al., "Evidence That Tumor Necrosis Factor a Converting Enzyme Is Involved in Regulated a-Secretase Cleavage of the Alzheimer Amyloid Protein Precursor," The Journal of Biological Chemistry, 273(43):27765-27767 (1998).

Caporaso et al., "Protein Phosphorylation Regulates Secretion of Alzheimer B/A4 Amyloid Precursor Protein," Proc. Natl. Acad. Sci. USA, 89:3055-3059 (Apr. 1992).

Carmeliet et al., "Growth properties and in vitro life span of Alzheimer disease and Down syndrome fibroblasts-a blind study", Mech. Aging Dev., vol. 53, pp. 17-33 (1990).

Chapman et al., "Genes, Models and Alzheimer's Disease," Trends in Genetics, 17(5) (May 2001).

Chen, RH. et al., "Nuclear Localization and Regulation of Erkand rsk Encoded Protein Kinases", Mol. Cell. Biol. 12,915-927 (1992).

Cheung et al., "Natural Variation in Human Gene Expression Assessed in Lymphoblastoid Cells," Nature Genetics, 33:422-425 (2003).

Christner, C., "FKBP Ligands as Novel Therapeutics for Neurological Disorders", Mini-Rev. Med. Chem. 1,377-397 (2001).

Chung, H. et al., "Protein Phosphatase 2A Suppresses MAP Kinase Signaling and Ectopic Protein Expression", Cell Signal. 11,575-580 (1999).

Clark et al.,, "Evidence that the Bradykinin-induced Activation of Phospholipase D and of the Mitogen-activated Protein Kinase Cascade Involve Different Protein Kinase C. Isoforms," J. Biol. Chem. 270:7097-7103, 1995.

Connolly, G.P., "Fibroblast Models of Neurological Disorders: Fluorescence Measurement Studies", Trends Pharmacol. Sci. 19, 171-177 (1998).

Cornforth et al., "Automated Classification Reveals Morphological Factors Associated with Dementia," Applied Computing, 8:182-190 (2008).

Cruzblanca et al., "Bradykinin Inhibits M Current via Phospholipase C and Ca2+ Release from IP3-sensitive Ca1 + Stores in Rat Sympathetic Neurons, " Proc. Natl. Acad. Sci. USA, 95:7151-7156 (Jun. 1998).

Cuenda et al., "Use of Kinase Inhibitors to Dissect Signaling Pathways," Methods in Molecular Biology,vol. 99, Humana Press Inc., Totowa, NJ (2000).

Cummings, J.L. et al., "Alzheimer's Disease: Etiologies, Pathophysiology, Cognitive Reserve, and Treatment Opportunities", Neurology 51, S2-S17 (1998).

De Leon et al., "Biomarkers for the early diagnosis of Alzheimer's disease," Neurology, 5 (Mar. 2006).

Dineley, Kit et al.,"Beta-amyloid Activates the Mitogen-activated Protein Kinase Cascade via Hippocampal alpha7 Nicotinic Acetylcholine Receptors: in vitro and in vivo Mechanism is Related to Alzheimer's Disease", J. Neurosci. 21,4125-4133 (2001).

Du et al., "Protein Kinase C Activators Work in Synergy with Specific Growth Factors to Initiate Tyrosine Hydroxylase Expression in Striatal Neurons in Culture," J. Neurochem. 1997; 68:564-69.

Dunckley et al., Gene Expression Correlates of Neurofibrillary Tangles in Alzheimer's Disease, Neurobiol Aging, 27(1):1359-1371 (2006).

Ekinci et al., "Hyperactivation of Mitogen-Activated Protein Kinase Increases Phosphyo-Tau Immunoreactivity Within Human

(56) References Cited

OTHER PUBLICATIONS

Neuroblastoma: Additive and Synergistic Influence of Alteration of Additional Kinase Activities," Cell Mol. Neurobiol., 19(2):249-260 (1999).
El-Dahr et al., "Bradykinin Stimulates the ERKfwdanwElk-1fwdanwFos/AP-1 Pathway in Nesagial Cells," American Journal of Pyschology, 275(3 Part w):F343-F352 (Sep. 1998).
Enard et al., "Intra- and Interspecific Variation in Primate Gene Expression Patterns," Science, 296(5566):340-343 (2002).
English-language Translation for JP 6-279311 dated Jun. 2008.
English-language Translation for JP10-90263 dated Apr. 10, 1998.
Est Profile Hs.400740, available at www.ncbi.nlm.nih.gov/UniGene, printed on Aug. 3, 2012, pp. 1-3.
Etchberrigaray et al., "Ionic and Signal Transduction Alterations in Alzheimer's Disease," Molecular Neurobiology, 20 (1999).
Etcheberrigaray et al., "Calcium Responses are Altered in Fibroblasts from Alzheimer's Patients and Pre-symptomatic PS1 Carriers; A Potential Tool for Early Diagnosis," Alzheimer's Reports, 3(5&6):305-312 (2000).
Etcheberrigaray et al., "Calcium Responses in Fibroblasts from Asymptomatic Members of Alzheimer's Disease Families," Neurobiol. Of Disease., 5:37-45 (1998).
Etcheberrigaray et al., "Potassium Channel Dysfunction in Fibroblasts Identifies Patients with Alzheimer Disease," Proc. Natl. Acad. Sci. USA, 90:8209-8213 (Sep. 1993).
Etcheberrigaray et al., "Therapeutic effects of PKC activators in Alzheimer's disease transgenic mice", PNAS, 01(30):11141-11146 (2004).
Etcheberrigary et al., "Molecular Mechanisms of Memory and the Pathophysiology of Alzheimer's Disease," Ann NY Acad Sci., 747:245-55 (1994).
European Search Report for EP 02 72 3236 dated Mar. 24, 2004.
Extended European Search Report in EP 13004274.0 dated Oct. 28, 2013.
Extended European Search Report issued on EP 08 02 0258 dated Jan. 30, 2009.
Extended European Search Report issued on EP 10 01 1288, dated Mar. 25, 2011.
Extended European Search Report issued on EP 10 01 1289 dated Mar. 23, 2011.
Extended European Search Report issued on EP 10 01 2836, dated Mar. 25, 2011.
Extended European Search Report issued on EP 10 011 290, dated Mar. 23, 2011.
Fan et al., "Arachidonic Acid and Related Methyl Ester Mediate Protein Kinase C Activation in Intact Platelets Through the Arachidonate Metabolism Pathways," Biochemical and Biophysical Research Communications, 169(3):933-940 (Jun. 29, 1990).
Favit et al., "Alzheimer's-specific effects of soluble β-amyloid on protein kinase C- and -degradation in human fybroblasts", Cell Biology, 95:5562-5567 (1998).
Fernandez, J. et al., "Okadaic Acid, Useful Tool for Studying Cellular Processes", Current Med. Chem. 9, 229-262 (2002).
Ferrell Jr., J.E., "How Regulated Protein Translocation can Produce Switch-like Responses", Trends Biochem. Sc. 23,461-465 (1998).
Final Office Action dated Sep. 13, 2011, in U.S. Appl. No. 11/660,868.
Final Office Action dated Oct. 11, 2011, in U.S. Appl. No. 12/083,056.
Force, T. et al., "Growth Factors and Mitogen-activated Protein Kinases", Hypertension 31, 152-161 (1998).
Frey et al. "Problems Associated with Biological Markers of Alzheimer's Disease," Neurochemical Research, 30(12):1501-1510 (Dec. 2005).
Furukawa et al., "Formation of Human Fibroblast Aggregates (Spheroids) by Rotational Culture", Cell Transplantation, vol. 10, pp. 441-445 (2001).
Gasparini et al., "Stimulation of β-Amyloid Precursor Trafficking by Insulin Reduces Intraneuronal β-Amyloid and Requires Mitogen-Activated Protein Kinase Signaling," The Journal of Neuroscience, 21(8):2561-2570 (Apr. 15, 2001).

Gebreyesus et al., "Bradykinin Elevates Tyrosine Hydroxylase and Dopamine Beta-Hydroxylase mRNA levels in PC12 Cells," Brain Research, 608(2):345-348 (1993).
Gibson et al., "Calcium stores in cultured fibroblasts and their changes with Alzheimer's disease," Biochimica et Biophysica Acta, 1316:71-77 (1996).
Gillespie et al., "Secretory Processing of the Alzheimer Amyloid B/A4 Protein Precursor is Increased by Protein Phosphorylation," Biochemical and Biophysical Research Communications, 187(3):1285-1290 (1992).
Goedert, M. et al., "Tau Proteins of Alzheimer Paired Helical Filaments: Abnormal Phosphorylation of All Six Brain Isoforms", Neuron 8, 159-168 (1992).
Gold, B.G., "FK506 and the Role of the Immunophilin FKBP-52 in Nerve Regeneration", Drug Metab. Rev. 31,649-663 (1999).
Gong et al., "Phosphorylation of Microtubule-Associated Protein Tau is Regulated by Protein Phosphatase 2A in Mammalian Brain," Jour. Of Biol. Chem., 275(8):5535-5544 (Feb. 25, 2000).
Gong, C.X. et al., "Phosphatase Activity Toward Abnormally Phosphorylated Tau; Decrease in Alzheimer Disease Brain", J. Neurochem. 65, 732-738 (1995).
Gonzales, EA et al., "Serum-induced Translocation of Mitogen-activated Protein Kinase to the Cell Surface Ruffling Membrane and the Nucleus", J. Cell Biol. 122, 1089-10101 (1993).
Govoni et al., "Cytosol Protein Kinase C Downregulation in Fibroblasts from Alzheimer's Disease Patients," Neurology, 43:2581-2586 (1993).
Grant et al., "Phosphorylation of Mitogen-Activated Protein Kinase is Altered in Neuroectoderman Cells Overexpressing the Human Amyloid Precursor Protein 751 Isoform," Molecular Brain Research., 72:115-120 (1999).
Greenberg et al., "Secreted Beta-amyloid Precursor Protein Stimulates Mitogen-activated Protein Kinase and Enhances Tau Phosphorylation," Proc Natl Acad Sci USA, 91:7104-7108 (1994).
Growdon et al., "Biomarkers of Alzheimer Disease", Arch Neurol., vol. 56, No. 3, pp. 281-283, 1999.
Guise, S. et al., "Hyperphosphorylation of Tau is Mediated by ERK Activation During Anticancer Drug-induced Apoptosis in Neuroblastoma Cells", J. Neurosci. Res. 63,257-267 (2001).
Haug et al., "Decreased Inositol (1 ,4,5)-Trisphosphate Receptor Levels in Alzheimer's Disease Cerebral Cortex: Selectivity of Changes and Possible Correlation to Pathological Severity," Neurodegeneration, 5:169-176 (1996).
Heid, C.A. et al., "Real Time Quantitative PCR," Genome Res. 6, 986-994 (1996).
Hetman et al., "Role of Extracellular Signal Regulated Kinases 1 and 2 in Neuronal Survival," Eur. J. Biochem, 271:2050-2055 (2004).
Hirashima et al., "Calcium Responses in Human Fibroblasts: A Diagnostic Molecular Profile for Alzheimer's Disease," Neurology of Aging, 17(4):549-555 (1996).
Hogervorst et al., "The Validity and Reliability of 6 Sets of Clinical Criteria to Classify Alzheimer's Disease and Vascular Dementia in Cases confirmed Post-Mortem: Added Value of a Decision Tree Approach," Dement Geriatr Coqn Disord 2003:16:170-180.
Hongpaisan et al., "A structural basis for enhancement of long-term associative memory in single dendritic spines regulated by PKC", Proc. Natl. Acad. Sci .USA, vol. 104, No. 49, pp. 19571-19576, Dec. 4, 2007.
Hoshikawa et al., "Hypoxia Induces Different Genes in the Lungs of Rats Compared with Mice," Physiol Genomics, 12:209-219 (2003).
House et al., "Protein kinase C contains a pseudosubstrate prototope in its regulatory domain." Science, vol. 238, No. 4834, pp. 1726-1728, Dec. 1987.
Huang et al., "Increased Inositol 1,4, 5-Trisphosphate Accumulation Correlates Withan Up-Regulation of Bradykinin Receptors in Alzheimer's Disease," Journal of Neurochemistry, 64(2):761-766 (Feb. 1995).
Huang et al., "Inositol Phosphates and Intracellular Calcium after Bradykinin Stilumation in Fibroblasts from Young, Normal Aged and Alzheimer Donors," Neurobiology of Aging, US, 12(5):469-473 (Sep. 1991).

(56) References Cited

OTHER PUBLICATIONS

Huang et al., "Involvement of Intermediary Metabolites in the Pathway of Extracellular Ca2+ Induced Mitogen-Activated Protein Kinase Activation in Human Fibroblasts," Cell. Signal, vol. 11, No. 4 pp. 263-274 (1999).
Hug et al.,"Protein kinase C isoenzymes: divergence in signal transduction?"Biochem J. 1993;291:329-343.
Huynh et al., "Reduced Protein Kinase C Immunoreactivity and Altered Protein Phosphorylation in Alzheimer's Disease Fibroblasts," Arch Neurol 46 (1989).
Hyman et al.,, "Extracellular Signal-Regulated Kinase (MAP Kinase) Immunoreactivity in the Rhesus Monkey Brain." Neuroscience Letters, 166:113-116 (1994).
International Preliminary Report on Patentability and Written Opinion for PCT/2005/036014 dated Apr. 24, 2008.
International Preliminary Report on Patentability and Written Opinion for PCT/2006/022156 dated Apr. 24, 2008.
International Preliminary Report on Patentability and Written Opinion for PCT/US2006/037186 dated Apr. 16, 2008.
International Search Report and Written Opinion for PCT/US2006/037186 dated Apr. 11, 2007.
International Search Report and Written Opinion for PCT/US2009/051927 dated Jan. 18, 2010.
International Search Report and Written Opinion issued in PCT/US2010/051112 dated May 9, 2011.
International Search Report and Written Opinion issued in PCT/US2010/051236 dated Mar. 2, 2011.
International Search Report and Written Opinion on PCT/US2005/036014 dated Oct. 19, 2006.
International Search Report and Written Opinion on PCT/US2006/022156 dated Feb. 8, 2007.
International Search Report for PCT/US2004/38160 dated Nov. 4, 2005.
International Search Report for PCT/US2009/051931 dated Nov. 4, 2009.
International Search Report issued on PCT/US2005/036014, published Apr. 19, 2007 (11 pages total).
International Search Report issued on PCT/US2006/022156, published Apr. 19, 2007, 6 pages.
International Search Report issued on PCT/US2009/002120, dated Sep. 25, 2009.
Irizarry et al., "Biomarkers of Alzheimer Disease in Plasma," The Journal of the American Society for Experimental NeuroTherapeutics, 1:226-234 (Apr. 2004).
Ito et al., "Internal Ca2+ Mobilization is Altered in Fibroblasts from Patients with Alzheimer Disease." Proc Natl Acad Sci USA, 91:534-538 (1994).
Janssens, V. et al., "Identification and Functional Analysis of Two Ca2+-Binding EF Hand Motifs in the B"/PR72 Subunit of Protein Phosphatase 2A", J. Biol. Chem. 278, 10697-10706 (2003).
Janssens, V. et al., "Protein Phosphatase 2A: A Highly Regulated Family or Serine/threonine Phosphatases Implicated in Cell Growth and Signaling",.Biochem. J. 353,417-439 (2001).
Jellinger, KA. et al., "Neuropathology of Alzheimer's Disease: a Critical Update", J. Neural Transm. Suppl. 54;77-95 (1998).
Jin et al., "Changes in Protein Kinases in Brain Aging and Alzheimer's Disease," Drugs &Aging, 6(2):136-149 (1995).
Johnson et al., "IQGAP1 regulation and roles in cancer", Cellular Signalling, vol. 21, pp. 1471-1478 (2009).
Kang et al., "The precursor of Alzheimer's disease amyloid A4 protein resembles a cell-surface receptor," Nature, 1987;325:733-736.
Kanno et al., "The Linoleic Acid Derivative DCP-LA Selectively Activates PKC-ε, Possibly Binding to the Phosphatidylserine Binding Site," Journal of Lipid Research, 47:1146-56 (2006).
Kanno et al., "The Newly Synthesized Linoleic Acid Derivative DCP-LA Selectively Activates PKC-ε", Dept. of Physiology, Hyogo College of Med., Hyogo, Japan, p. 552 (2006).
Katzman, "Alzheimer's disease," New England. Journal of Medicine. 1986;314:964-973.

Khan et al., "A Cellular Model of Alzheimer's Disease Therapeutic Efficacy: PKC Activation Reverses a Beta-Induced Biomarker Abnormality on Cultured Fibroblasts," Neurobiology of Disease, 34(2): 332-339, vol. 34, No. 2 (May 2009).
Khan et al., "An Internally Controlled Perifpheral Biomarker for Alzheimer's Disease: Erk1 and Erk2 responses to the Inflammatory Signal Bradykinin," PNAS, vol. 103, No. 35, pp. 13203-13207, Aug. 29, 2006.
Kikkawa et al., "The Protein Kinase C Family: Heterogeneity and its Implications." Ann. Rev. Biochem, vol. 58, pp. 31-44, 1989.
Kilpatrick et al., "Regulation of TNF Mediated Antiapoptoptic Signaling in Human Neutrophils: Role of-PKC and ERK1/2," Journal of Leukocyte Biology, 80:1512-1521 (Dec. 2006).
Kins, S. et al., "Reduced Protein Phosphatase 2A Activity Induces Hyperhosphorylation and Altered Compartmentalization of Tau in Transgenic Mice", J. Biol. Chem. 276, 3819338200 (2001).
Kitaguchi et al., "Novel precursor of Alzheimer's disease amyloid protein shows protease inhibitory activity," Nature, 1988; 331:530-532.
Kleinman et al., "Use of extracellular matrix components for cell culture", Analytical Biochemistry, 166, pp. 1-13, (1987).
Klettner, A. et al.,"The Neuroprotective Actions of FK506 Binding Protein Ligands: Neuronal Survival is Triggered by de novo RNA Synthesis, but is Independent of Inhibition of JNK and Calcineurin", Mol. Brain Res. 97, 21-31 (2001).
Knowles, R.B. et al., "Demonstration by Fluorescence Resonance Energy Transfer of a Close Association Between Activated MAP Kinase and Neurofibrillary Tangles: Implications for MAP Kinase Activation in Alzheimer Disease", J. Neuropathol. Exp. Neurol. 58,1090-1098 (1999).
Kohkhlatchev, AV. et al., "Phosphorylation of the MAP Kinase ERK2 Promotes its Homodimerization and Nuclear Translocation", Cell 93, 605-615 (1998).
Kurumatani et al., "Loss of Inositol 1,4,5-trisphosphate Receptor Sites and Decreased PKC Levels Correlate with Staging of Alzheimer's Disease Neurofibrillary Pathology," Brain Research, 796:209-221 (1998).
Kuzirian et al., "Bryostatin Enhancement of Memory in Hermissenda", Biol. Bull. 210:201-214 (Jun. 2006).
L'Allemain, "Deciphering the Map Kinase Pathway," Progress in Growth Factor Research, 5(3):291-334 (Jan. 1, 1994).
Lallemend et al., I., "Activation of protein kinase CBI constitutes new neurotrophic pathway for deafferented spiral ganglion neurons," J. Cell Sci. 2005;118:4511-25.
Laporte et al., "Role of ERK MAP Kinases in Responses of Cultured Human Airway Smooth Muscles Cells to IL-1B." Am. J. Physiol. Lung Cell Mol. Physiol., 277:943-951 (1999).
Laurent-Matha et al., "Catalytically inactive human cathepsin D triggers fibroblast invasive growth", Journal of Cell Biology, vol. 168, No. 3, pp. 489-499, Jan. 31, 2005.
Lee, V.M., "Disruption of the Cytoskeleton in Alzheimer's Disease", Current Opin. Neurobiol..5,663-668 (1995).
Leissring et al., "Capacitative Calcium Entry Deficits and Elevated Luminal Calcium Content in Mutant Presenilin-1 Knockin Mice," The Journal of Cell Biology, 149 (2000).
Leissring et al., "Presenilin-2 Mutations Modulate Amplitude and Kinetics of Inositol 1,4,5-Trisphosphate-mediated Calcium Signals," The Journal of Biological Chemistry, 274(46):32535-32538 (Nov. 12, 1999).
Lenormand, P. et al., "Growth Factors Induce Nuclear Translocation of MAP Kinase (p42mapk and p44mapk) But Not of Their Activator MAP Kinase Kinase (p45mapkk) in Fibroblasts", J. Cell Biol. 122, 1079-1088 (1993).
Lewis, T.S. et al., "Signal Transduction Through MAP Kinase Cascades", Adv. Cancer Res. 74,49-139 (1998).
Liang et al., "Altered Neuronal Gene Expression in Brain Regions Differentially affected by Alzheimer's Disease: A reference Data Chart," Physiol Genormics, 33:240-256 (2008).
Liebmann, C., "Bradykinin Signaling to MAP Kinase: Cell Specific Connections Versus Principle Mitogenic Pathways", Biol. Chem. 382, 49-55 (2001).
Liu et al., "Protein Phasphatase 2A in Alzheimer's Disease," Pathophysiology 16:273-277 (2009).

(56) References Cited

OTHER PUBLICATIONS

Liu et al., "The Sevenfold Way of PKC Regulation," Cellular Signalling,10(8):529-42 (1998).
Liu et al., Cellular Signalling,10(8):529-42.
Livak, KJ. et al., "Analysis of Relative Gene Expression Data Using Realtime Quantitative PCR and the 2-AAC T Method", Methods. 25, 402-408 (2001).
Loring et al., "A Gene Expression Profile of Alzheimer's Disease," DNA and Cell Biology, 20(11):683-695 (2001).
Lu et al., P44mpk MAP Kinase Induces Alzheimer Type Alterations in Tau Function and in Primary Hippocampal Neurons, J. Neurosci. Res., 35:439-444 (1993).
Luigi et al., "Inflammatory Markers in Alzheimer's Disease and Multi-Infarct Dementia," Mechanisms of Ageing and Development, 122:1985-1995 (2001).
Mandelkow, E. et al. "On the Structure of Microtubules, Tau, and Paired Helical Filaments", Neurobiol. Aging 16, 347-354 (1995).
Masliah et al., "Differential Involvement of Protein Kinase C Isozymes in Alzheimer's Disease," The Journal of Neuroscience,10:7, 2113-2124, Jul. 1990.
Masliah, "Protein Kinase C Alteration Is an Early Biochemical Marker in Alzheimer's Disease," The Journal of Neuroscience, 11(9): 2759-2767 (1991).
Matsubayash, Y. et al.,"Evidence for Existence of a Nuclear Pore Complex-mediated, Cytosol-independent Pathway of Nuclear Translocation of ERK MAP Kinase in Permeabilized Cells", J. Biol. Chem. 276, 41755-41760 (2001).
Mattson et al., "Presenilin-1 Mutation Increases Neuronal Vulnerability to Focal Ischemia in Vivo and to Hypoxia and Glucose Deprivation in Cell Cuture: Involvement of Perturbed Calcium Homeostatis," The Journal of Neuroscience, 20(4):1358-1364 (Feb. 15, 2000).
Mattson, M. et al., "Presenilin Mutations and Calcium Signaling Defects in the Nervous and Immune Systems", BioEssays 23.8, 733-744.
McCoy et al., "Serum-and bradykinin-induced calcium transients in familial alzheimer's fibroblasts," Neurobiology of Aging, 14(5):447-455 (Sep.-Oct. 1993).
McDonald et al., "β-Amyloid Fibrils Activate Parallel Mitogen-Activated Protein Kinase Pathways in Microglia and THP1 Monocytes," J Neurosci, 18:4451-4460 (1998).
McMahon, KA. et al.,"Colony-stimulating Factor-1 (CSF-1) Receptor-mediated Macrophase Differentiation in Myeloid Cells: A Role for Tyrosine 559-dependent Protein Phosphatase 2A (PP2A) Activity", Biochem. J. 358,431-436 (2001).
Michiels et al., "Prediction of Cancer Outcome with Microarrays: A multiple Random Validation Strategy," Lancet, 365:488-492 (2005).
Nagao, M. et al., "Protein Serine/threonine Phosphatase as Binding Proteins for Okadaic Acid", Mutat. Res. 333,173-179 (1995).
Nagasaka et al., "A Unique Gene Expression Signature Discriminates Familial Alzheimer's Disease Mutation Carriers from their Wild-type Siblings,", Proc. Natl. Acad. Sci., 102(41):14854-14859 (2005).
Nagata et al., "FR236924, a Newly Synthesized Derivataive of Linoleic Acid, Ameliorates Memory Deficits in Rats Intraventricularly Injected with Amyloid-Beta Peptide." Jpn. J. Physiol. 53,Suppl. 2003(319): S261.
Nagata et al., "The Newly Synthesized Linoleic Acid Derivative CP-LA Ameliorates Memory Deficits in Animal Dmodels Treated with Amyloid-β Peptide and Scopolamine", Psychogeriatrics, 5:22-126 (2003).
Neve et al., "Alzheimer's Disease: Dysfunction of a Signalling Pathway Mediated by the Amyloid Precursor Protein?" Biochem. Soc. Symp. 67:37-50, (No Year Provided).
Ning et al., "Early Response Gene Signalling in Bryostatin-Stimulated Primary B Chronic Lymphocytic Leukaemia Cells in Vitro," Biochemical Journal, 319(1):59-65 (1996).
NME Digest, Drug News Perspect, 2002, pp. 666-674, vol. 15, No. 10.
Oddo et al., "Temporal Profile of Amyloid-β (AB) Oligomerization in an in Vivo Model of Alzheimer Disease—A Link Between AB and TAU Pathlogy," Journal of Biological Chemistry, 281(3):1599-1604 (Jan. 20, 2006).
Office Action (Final) dated May 19, 2015 in U.S. Appl. No. 12/895,957.
Office Action (Final) dated Nov. 20, 2015, in U.S. Appl. No. 13/774,049.
Office Action (final) dated Oct. 17, 2013, in U.S. Appl. No. 12/729,042.
Office Action (Restriction Requirement) dated Aug. 16, 2011, in U.S. Appl. No. 12/510,707.
Office Action (Restriction Requirement) dated Dec. 2, 2010, in U.S. Appl. No. 12/083,056.
Office Action (Restriction Requirement) dated May 23, 2011, in U.S. Appl. No. 12/510,681.
Office Action (Restriction Requirement) dated Oct. 27, 2010, in U.S. Appl. No. 12/729,042.
Office Action dated Aug. 24, 2012, in U.S. Appl. No. 12/083,056.
Office Action dated Dec. 12, 2010, in U.S. Appl. No. 11/660,868.
Office Action dated Jan. 2, 2014, in U.S. Appl. No. 12/729,042.
Office Action dated Mar. 25, 2014, in U.S. Appl. No. 12/895,957.
Office Action dated Oct. 11, 2012, in Application No. 12/896,862.
Office Action dated Sep. 20, 2012, in U.S. Appl. No. 12/729,042.
Office Action (Final) dated Jun. 13, 2014 in U.S. Appl. No. 13/401,459.
Office Action (non-final) dated Nov. 5, 2014, in co-pending U.S. Appl. No. 12/895,957.
Office Action (Requirement for Restriction) dated Aug. 12, 2010, in U.S. Appl. No. 11/660,868.
Office Action dated Apr. 29, 2011, in U.S. Appl. No. 12/083,056.
Office Action dated Aug. 17, 2012, in U.S. Appl. No. 11/660,868.
Office Action dated Aug. 2, 2013, U.S. Appl. No. 12/510,707.
Office Action dated Dec. 9, 2016, U.S. Appl. No. 14/803,762.
Office Action dated Feb. 12, 2016, in U.S. Appl. No. 12/895,957.
Office Action dated Jul. 31, 2013, in U.S. Appl. No. 13/401,459.
Office Action dated Jun. 7, 2011, in U.S. Appl. No. 12/729,042.
Office Action dated Mar. 3, 2015, U.S. Appl. No. 13/774,049.
Office Action dated Nov. 15, 2012, in U.S. Appl. No. 12/510,707.
Office Action dated Nov. 18, 2013, in U.S. Appl. No. 12/895,957.
Ohta et al., "Stearic Acid Facilities Hoppocampal Neurotransmission by Enhancing Micotinic Ach Receptor Responses via an PKC Pathway," Molecular Brain Research, 119:83-89 (Aug. 27, 2003).
Pascale et al., "Enhanced BK-Induced Calcium Responsiveness in PC12 Cells Expressing the C100 Fragment of the Amyloid Precursor Protein," Brain Res Mol Brain Res, 72:205-2 (1999).
Pasinetti GM., "Use of cDNA Microarray in the Search for Molecular Markers Involved in the Onset of Alzheimer's Disease Dementia", J Neurosci Res., 65(6):471-476, Aug. 31, 2001.
Pei et al., "Expression of Protein Phasphatases (PP-1, PP-2A, PP-2B, and PTP-1B) and Protein Kinases (MAP kinase and P34cdc2) in the Hippocampus of Patients with Alzheimer Disease and Normal Aged Individuals," Brain Research, 665(1-2):70-76 (Aug. 29, 1994).
Planel, E. et al., "Inhibition of Protein Phosphatase 2A Overrides Tau Protein Kinase I/glycogen Synthase Kinase 3β and Cyclin Dependent Kinase 5 inhibition and Results in Tau Hyperphosphorylation in the Hippocampus of Starved Mouse", J. Biol. Chern. 276, 34298-34306 (2001).
Ponte et al., "A new A4 amyloid mRNA contains a domain homologous to serine proteinase inhibitors," Nature, 1988;331:525-527.
PUB CHEM Compound, XP002550143 (May 27, 2005).
Putney, Jr., "Presenilins, Alzheimer's Disease, and Capacitative Calcium Entry," Neuro, 27:411-412 (2000).
Racchi et al., "Bradykinin-induced amyloid precursor protein secretion: a protein kinase C-independent mechanism that is not altered in fibroblasts from patients with sporadic Alzheimer's disease", Biochem J., vol. 330, pp. 1271-1275, 1998.
Rametti et al., "Linking Alterations in Tau Phosphorylation and Cleavage during Neuronal Apoptosis*," The Journal of Biological Chemistry, 279(52):54518-54528 (2004).

(56) References Cited

OTHER PUBLICATIONS

Rapoport et al., "PD98059 Prevents Neurite Degeneration Induced by Fibrillar B-Amyloid in Mature Hippocampal Neurons", J. Neurochem., vol. 74, pp. 125-133, 2000.
Remarque et al., "Patients with Alzheimer's Disease Display a Pro-inflammoatory Phenotype," Experimental Gerontology, 36:171-176 (2001).
Reynolds et al., "Phosphorylation Sites on Tau Identified by Nanoelectrospray Mass Spectrometry:Differences in Vitro Between the Mitogen-Activated Protein Kinase ERK2, c-Jun N-Terminal Kinase and 0 P38, and Glycogen Synthase Kinase-3B," J. Neurochem., 74:1587-1595 (2000).
Roovers, K. et al., "Integrating the MAP Kinase Signal into the G1 Phase Cell Cycle Machinery", Bioessays 22, 818-826 (2000).
Roux et al., "ERK and p38 MAPK-Activated Protein Kinases: a Family of Protein Kinase with Diverse Biological Functions," Microbiology and Molecular Biology Reviews, 68(2):320-344 (Jun. 2004).
Saito, T. et al., "In Situ Dephosphorylation of Tau by Protein Phosphatase 2A and 2B in Fetal Rat Primary Cultured Neurons", FEBS Lett. 376,238-242 (1995).
Sato et al., "Elevated Amyloid Beta Protein (1-40) Level Induces CREB Phosphorylation at Serine-133 via p44/42 MAP kinase (Erk1/2)-dependent pathway in rat pheochromocytoma PC12 cells," Biochemical and Biophysical Research Communications, 232(3):637-642(Mar. 27 1997).
Shaw et al., "Biomakers of neurodegeneration for diagnosis and monitoring therapeutics", Natures Review Drug Discovery, vol. 6, pp. 295-303 (2007).
Sheehan et al., "Calcium Homeostasis and Reactive Oxygen Species Production in Cells Transformed by Mitochondria from Individuals with Sporadic Alzheimer's Disease," The Journal of Neuroscience, 17(12):4612-4622 (Jun. 15, 1997).
Sheppeck, J.E. et al., "Inhibition of the Ser-Thr Phosphatases PPI and PP2A by Naturally Occurring Toxins", Bioorg. Med. Chem. 5, 1739-1750 (1997).
Silverstein, A.M. et al., "Actions of PP2A on the MAP Kinase Pathway and Apoptosis are Mediated by Distinct Regulatory Subunits", Proc. Natl. Acad. Sci. USA 99,4221-4226 (2002).
Solerte et al., "Hemorheological Changes and Overproduction of Cytokines from Immune Cells in Mild to Moderate Dementia of the Alzheimer's Type: Adverse Effects on Cerebromicrovascular System," Neurobiology of Aging, 21( 2):271-287 (2000).
Sun et al., "Poststroke neuronal rescue and synaptogenesis mediated in vivo by protein kinase C in adult brains", Proc. Natl. Acad. Sci. USA, Sep. 9, 2008; vol. 105, No. 36, pp. 13620-13625.
Sun et al., "Dual Effects of Bryostatin-1 on Spatial Memory and Depression", Eur. J. Pharmacol., vol. 512, pp. 43-51, 2005.
Sweatt, J.D., "The Neuronal MAP Kinase Cascade: a Biochemical Signal Integration System Subserving Synaptic Plasticity and Memory", J. Neurochem. 76,1-10 (2001).
Tanaka et al., "The Newly Synthesized Linoleic Acid Derivative FR236924 Induces a Long-Lasting Facilitation of 4 Hippocampal Neurotransmission by Targeting Nicotinic Acetylcholine Receptors", Bioorganic & Medicinal Chem. Letters, 13:1037-1040 (2003).
Tanzi et al., "Protease Inhibitor domain encoded by an amyloid protein precursor mRNA associated with Alzheimer's disease," Nature, 1988; 331:528-530.
Tanzi et al., "The Gene Defects Responsible for Familial Alzheimer's Disease," Neurolobiology of Disease, 3:159-168 (1996).
Tesco et al., "Growth properties of familial Alzheimer skin fibroblasts during in vitro aging", Exp Gerontology, 28(1):51-8, 1993.
Thal et al., "The Role of Biomarkers in Clinical Trials for Alzheimer Disease," Alzheimer Dis Assoc Disord, 20(1) Jan.-Mar. 2006.
Treisman, R, "Regulation of Transcription by MAP Kinase Cascades", Curro Opin. Cell Biol. 8, 205-215 (1996).
Urbanelli et al., "Cathepsin D expression is decreased in Alzheimer's disease fibroblasts", Neurobiology of Aging, vol. 29, pp. 12-22 (2008).

Valijent, E. et al., "Mitogen-activated Protein Kinase/extracellular Signal-regulated Kinase Induced Gene Regulation in Brain: A Molecular Substrate for Learning and Memory", Mol. Neurobiol. 23, 83-99 (2001).
Vogelsberg-Ragaglia et al., "PP2A mRNA Expression is Quantitatively Decreased in Alzheimer's Disease Hippocampus1 ," Experimental Neurology, 168:402-412 (2001).
Volmat, V. et al., "The Nucleus, a Site for Signal Termination by Sequestration and Inactivation of p42/p44 MAP Kinases", J. Cell Sci. 114,3433-3443 (2001).
Wallace, "Effects of Alzheimer's Disease-related $\beta$ amyloid protein fragments on enzymes metabolizing phosphoinositides in brain," Biochem Biophys Acta., 1227:183-187 (1994).
Wang, J.Z. et al., "Dephosphorylation of Alzheimer Paired Helical Filaments by Protein Phosphatase-2A and -2B", J. Biol. Chem. 270, 4854-4860 (1995).
Weeraratna et al., "Alterations in immunological and neurological gene expression patterns in Alzheimer's disease tissues", vol. 313, pp. 450-461 (2007).
Weinreb et al., "Neuroprotection via pro-survival protein kinase C isoforms associated with Bcl-2 family members," The FASEB Journal 2004; 118:1471-1473.
Winer, J. et al., "Development and Validation of Real-time Quantitative Reverse Transcriptase-polymerase Chain Reaction for Monitoring Gene Expression in Cardiac Myocytes in vitro", Anal. Biochem. 270, 41-49 (1999).
Winter, C. et al., "MAP Kinase Phosphatase 1 is Expressed and Enhanced by FK506 in Surviving Mamillary, but not Degenerating Nigral Neurons Following Anatomy", Brain Res. 801, 198-205 (1998).
Yaguchi et al., "Effects of Cis-unsaturated Free Fatty Acids on PKC-$\epsilon$ Activation and Nicotinic ACh Receptor Responses", Molecular Brain Res., 133:320-324 (2005).
Yaguchi et al., "Linoleic Acid Derivative DCP-LA Improves Learning Impairment in SAMP8", Neuropharmacology and Neurotoxicology, 17(1):105-108 (Jan. 23, 2006).
Yaguchi et al., "The CIS-Unsaturated Free Fatty Acid Derivative HEPBA Regulates $\alpha$7 Nicotinic ACh receptor Trafficing", Dept. af Physiology, Hyogo College of Med., Hyogo, Japan, Bulletin of the Japanese Society for Neurochemistry, 2008, 47(2/3): 222, Abstract O1-3.
Yamamoto et al., "The Linoleic Acid Derivative FR236924 Facilitates Hippocampal Synaptic Transmission by Enhancing Activity of Presynaptic $\alpha$7 Acetylcholine Receptors on the Glutamatergic Terminals", Neuroscience, 130:207-213 (2005).
Yang et al., "Bradykinin-Induced p42/p44 MAPK Phosphorylation and Cell Proliferation via Src, EGF Receptors and P13-K/Akt in Vascular Smooth Muscle Cells," Journal of Cellular Physiology, 203:538-546 (2005).
Yoo et al., "Presenilin-Mediated Modulation of Capacitative Calcium Entry," Neuron, 27:561-572 (Sep. 2000).
Youdim et al., "Molecular Basis of Neuroprotective Activities of Rasagiline and the Anti-Alzheimer Drug TV3326 [(N-Propargyl-(3R)Aminoindan-5-YL)-Ethyl Methyl Carbamate]," Cellular and Molecular Neurobiology, 21(6): 555-573 (Dec. 2001).
Young, et al., "Decreased Brain [3H]inositol1 ,4,5-trisphosphate Binding in Alzheimer's Disease," Neuroscience Letters, 94:198-202 (2000).
Zawadzka, M. et al., "Immunosuppressant FK506 Affects Multiple Signaling Pathways and Modulates Gene Expression in Astrocytes", Mol. Cell. Neurosci.22,202-209 (2003).
Zhang et al., "Oxidative Stress Differentially Modulates Phosphorylation of ERK, p38 and CREB Induced by NGF or EGF in PC12 Cells." Neurobiology of Aging, 20:271-278 (1999).
Zhao et al., "Brain Insulin Receptors and Spatial Memory—Correlated Changes in Gene Expression, Tyrosine Phosphorylation, and Signaling Molecules in the Hippocampus of Water Maze Trained Rats," The Journal of Biological Chemistry, 274(49):34893-34902 (1999).
Zhao et al., "Dysfunction of MAP Kinase signaling in Alzheimer's Disease," Society of Neuroscience, Abstracts 25, 31st Annual Meeting of the Society of Neuroscience, San Diego, CA, USA, 27(1):924, (Nov. 10-15, 2001).

(56) References Cited

OTHER PUBLICATIONS

Zhao et al., "Impairment of Phosphatase 2A Contributes to the Prolonged MAP Kinase Phosphorylation in Alzheimer's Disease Fibroblasts," Neurobiology of Disease, 14(3):458-469 (Dec. 2003).
Zhao et al., "MAP Kinase Signaling Cascade Dysfunction Specific to Alzheimer's Disease in Fibroblasts," Neurobiology of Disease, 11(1):166-183 (Oct. 2002).
Zhu et al., "The role of mitogenactivated protein kinase pathways in Alzheimer's disease," Neurosignals, 11(5):270-281, Sep. 2002.
European Search Report dated Oct. 1, 2018, corresponding to counterpart European Application No. 18172435.2; 19 pages.
Beil et al., "Helicobacter pylori fatty acid cis 9,10-methyleneoctadecanoic acid increases [Ca2+]i, activates protein inase C and stimulates acid secretion in parietal cells," Prostagiandins, Leukotrienes and Essential Fatty Acids, vol. 59, No. 2, (1998); pp. 119-125.
Beil et al., The Helicobacter pylori fatty acid cis-9, 10-methyleneoctadecanoic acid simulates protein kinase C and ncreases DNA synthesis of gastric HM02 cells, British Journal of Cancer, vol. 77, No. 11, (1998); pp. 1852-1856.
Mattern, "Preparation of Functional Group Analogs of Unsaturated Fatty Acids and Their Effects on the Circadian Rhythm of a Fatty-Acid-Deficient Mutant of Neurospora Crassa," Chemistry and Physics of Lipids, vol. 37 (1985), Elsevier Scientific Publishers Ireland Ltd.; pp. 297-306.
Vitali et al., "Molecular and phenotypic traits of in-vitro-selected mutants of Bifidobacterium resistant to rifaximin," International Journal of Antimicrobial Agents, vol. 31, (2008), Elsevier; pp. 555-560.
European Extended Search Report dated Jan. 11, 2019 received in European Patent Application No. 18 17 2435.2.

\* cited by examiner

PKC-ACTIVATING COMPOUNDS FOR THE TREATMENT OF NEURODEGENERATIVE DISEASES

This is a divisional application of U.S. application Ser. No. 13/401,459, filed Feb. 21, 2012, which is a continuation of U.S. application Ser. No. 12/510,681, filed Jul. 28, 2009, and claims the benefit of U.S. Provisional Application No. 61/084,172, filed on Jul. 28, 2008, all of which are incorporated herein by reference.

FIELD OF THE INVENTION

The present invention relates to compositions and methods to activate an isoform of protein kinase C (PKC). The present invention also provides methods for reducing neurodegeneration and for treatment of neurological diseases including Alzheimer's disease and stroke.

BACKGROUND OF THE INVENTION PKC

Activators in Alzheimer's Disease, Stroke, and Depressive Disorders

Alzheimer's disease (AD) is a neurodegenerative disorder characterized by the progressive decline of memory and cognitive functions. Dementia associated with AD is referred to as senile dementia of the Alzheimer's type (SDAT) in usage with Alzheimer's disease. AD is characterized clinically by progressive loss of memory, cognition, reasoning, judgment, and emotional stability that gradually leads to profound mental deterioration and ultimately, death. Although there are many hypotheses for the possible mechanisms of AD, one central theory is that the excessive formation and accumulation of toxic beta-amyloid (Aβ) peptides either directly or indirectly affects a variety of cellular events and leads to neuronal damage and cell death. Selkoe, *Neuron.* 1991; 6(4):487-98 1991; Selkoe, *J. Clin Invest.* 2002; 110(10): 1375-81.

AD is a progressive disorder with a mean duration of around 8-15 years between onset of clinical symptoms and death. AD is believed to represent the seventh most common medical cause of death and affects about 5 million people in the United States. The prevalence is expected to reach 7.7 million by 2030. About 1 in 8 people over the age of 65, 13% of this population, have AD (Alzheimer's Association 2008 Alzheimer's Disease Facts and Figures). AD currently affects about 15 million people world-wide (including all races and ethnic groups) and owing to the relative increase of elderly people in the population its prevalence is likely to increase over the next two to three decades. AD is at present incurable.

Protein kinase C (PKC) is one of the largest gene families of protein kinase. Several PKC isozymes are expressed in the brain, including PKC, PKCβ1, PKCβII, PKCδ, PKCε, and PKCγ. PKC is primarily a cytosolic protein, but with stimulation it translocates to the membrane. PKC has been shown to be involved in numerous biochemical processes relevant to Alzheimer's disease. PKC activation also has a crucial role in learning and memory enhancement and PKC activators have been shown to increase memory and learning. Sun and Alkon, *Eur J Pharmacol.* 2005; 512:43-51; Alkon et al., *Proc Natl Acad Sci USA.* 2005; 102:16432-16437. PKC activation also has been shown to induce synaptogenesis in rat hippocampus, suggesting the potential of PKC-mediated antiapoptosis and synaptogenesis during conditions of neurodegeneration. Sun and Alkon, *Proc Natl Acad Sci USA.* 2008; 105(36): 13620-13625. Postischemic/hypoxic treatment with bryostatin-1, a PKC activator, effectively rescued ischemia-induced deficits in synaptogenesis, neurotrophic activity, and spatial learning and memory. Sun and Alkon, *Proc Natl Acad Sci USA.* 2008. This effect is accompanied by increases in levels of synaptic proteins spiniophilin and synaptophysin and structural changes in synaptic morphology. Hongpaisan and Alkon, *Proc Natl Acad Sci USA.* 2007; 104:19571-19576. Bryostatin-induced synaptogenesis for long-term associative memory is also regulated by PKC activation. Hongpaisan and Alkon, *PNAS* 2007. PKC also activates neurotrophin production. Neurotrophins, particularly brain-derived neurotrophic factor (BDNF) and nerve growth factor (NGF), are key growth factors that initiate repair and regrowth of damaged neurons and synapses. Activation of some PKC isoforms, particularly PKCε and PKCα, protect against neurological injury, most likely by upregulating the production of neurotrophins Weinreb et al., *FASEB Journal.* 2004; 18:1471-1473). PKC activators are also reported to induce expression of tyrosine hydroxylase and induce neuronal survival and neurite outgrowth. Du and Iacovitti, *J. Neurochem.* 1997; 68: 564-69; Hongpaisan and Alkon, PNAS 2007; Lallemend et al., J. Cell Sci. 2005; 118: 4511-25.

AD is also characterized by tau hyperphosphorylation. Tau is expressed mainly in the brain, where it regulates the orientation and stability of microtubules in neurons, astrocytes and oligodendrocytes. In AD, normal soluble tau is transformed into insoluble paired helical filaments. This is linked to the post-translational change in tau, primarily the hyperphosphorylation of tau by a number of protein kinases. Studies have shown that synthetic Aβ promotes tau phosphorylation through activation of glycogen synthase kinase-3 GSK-3. Wang et al, *Journal of Neurochemistry.* 2006; 98(4): 1167-1175. Activation of PKC has been shown to protects rat primary hippocampal neurons from Aβ-mediated neurotoxicity, through inhibition of GSK-3β. Garrido et al., *FASEB J.* 2002: 1982.

PKC also activates TNF-alpha converting enzyme (TACE, also known as ADAM17), which is an enzyme that is involved in the proteolytic conversion of membrane-bound amyloid precursor protein (APP) to its non-pathogenic soluble form, known as soluble APP-alpha or sAPPα. Alkon et al., *Trends in Pharmacological Sciences.* 2007; 28(2): 51-60; Hurtado et al, *Neuropharmacology.* 2001; 40(8): 1094-1102. These sAPPα-producing enzymes are referred to generically as alpha-secretases. Activation of TACE by PKC also reduces cellular levels of pathogenic Aβ, which is produced by cleavage of APP by the beta-secretase enzyme (BACE). This is likely due to the fact that the TACE cleavage site is within the Aβ domain of APP. Overexpression of PKCδ has been shown to selectively increase the activity of endothelin-converting enzyme (ECE), which degrades Aβ. Choi et al, *Proc. Natl Acad. Sci. USA.* 2006; 103(21): 8215-8220. In addition, sub-nanomolar concentrations of bryostatin and a potent synthetic analog (picolog), both PKC activators, were found to cause stimulation of non-amyloidogenic pathways by increasing TACE and thus lowering the amount of toxic Aβ produced. Khan et al., *Proc. Natl. Acad. Sci. USA.* 2009; 34(2):332-9.

Reduction of Aβ levels is a major therapeutic goal in Alzheimer's disease. It has been speculated that inhibition of Aβ formation by PKC activators may be caused by competition of TACE and BACE for their common substrate, APP.

The strategy of PKC-mediated activation of a-secretases has the advantage of three parallel beneficial consequences in AD: increasing production of sAPP-α and reducing Aβ, enhancing memory via PKC-mediated phosphorylation of downstream substrates, and decreasing phosphorylation of tau through inhibition of GSK-3β.

AD patients already have reduced levels of PKCα/ε-mediated phosphorylation of Erk 1/2, a major downstream substrate of PKC. Khan and Alkon, *Proc Natl Acad Sci USA*. 2006; 103:13203-13207. In addition, Aβ application to normal fibroblasts reduces PKC activity because Aβ directly down-regulates PKC α/ε. PKC activators, especially those specific for PKC α/ε, would counteract the effect of Aβ and thereby reverse or prevent the Aβ-induced changes.

Stroke is a leading cause of disability and death in the United States, yet limited therapeutic options exist. Several PKC isoforms have been shown to have a central role in mediating ischemic and reperfusion damage following stroke. Studies with experimental stroke models, mouse genetics, and selective peptide inhibitors and activators have demonstrated that PKCε is involved in induction of ischemic tolerance and prevents damage, while PKCδ and γ are implicated in injury. Takayoshi et al., *Stroke*. 2007; 38(2): 375-380; and Bright et al., *Stroke*. 2005; 36: 2781. One possible mechanisms for PKCε's protective ischemic effect is that PKCε maintaining mitochondrial function via ERK activity and by mediating adenosine-induced mitochondrial ATP-sensitive potassium channels. Another potential mechanism is that PKCε elicits a neuroprotective effect via COX-2 induction. Kim et al., *Neuroscience*. 2007; 145(3): 931-941. Prostaglandin E2 (PGE2), the product of COX-2 activity, leads to neuroprotection in cerebral ischemia. As mentioned above, postischemic/hypoxic treatment with bryostatin-1, a PKC activator, effectively rescued ischemia-induced deficits in synaptogenesis, neurotrophic activity, and spatial learning and memory. Sun and Alkon, *Proc Natl Acad Sci USA*. 2008; 105(36): 13620-13625.

Circulating Aβ protein has been shown to be elevated in patients with acute ischemic stroke Circulating Aβ1-40 level was markedly elevated in ischemic stroke patients, as compared to controls. Lee et al., *Journal of Neural Transmission*. 2005; 112(10): 1371-79. A strong positive association between progressively accumulating vascular Aβ and augmentations in arteriole and frontal cortex wall thickness AD patients also has been shown, suggesting that the continually progressing Aβ-associated angiopathy, at the arteriolar level, harms the contractile apparatus and cerebral blood flow autoregulation, thereby making the downstream capillaries vulnerable to damage. Stopa et al., *Stroke*. 2008; 39:814.

In addition, some forms of stroke are caused by Aβ, such as those associated with cerebral amyloid angiopathy, also known as congophilic amyloid angiopathy (CAA). This disorder is a form of angiopathy in which the same Aβ deposits as found in AD accumulate in the walls of the leptomeninges and superficial cerebral cortical blood vessels of the brain. Amyloid deposition predisposes these blood vessel to failure, increasing the risk of a hemorrhagic stroke. CAA is also associated with transient ischemic attacks, subarachnoid hemorrhage, Down syndrome, post irradiation necrosis, multiple sclerosis, leucoencephalopathy, spongiform encephalopathy, and dementia pugilistica.

Evidence suggests that PKCα and ε are the most important PKC isoforms in eliciting the aforementioned beneficial effects in AD, stroke, and depressive disorders. Antisense inhibition of PKCα has been shown to block secretion of sAPPα, while PKCε is the isozyme that most effectively suppresses Aβ production. Racci et al., *Mol. Psychiatry*. 2003; 8:209-216; and Zhu et al., *Biochem. Biophys. Res. Commun.* 2001; 285: 997-1006. Thus, isoform specific PKC activators are highly desirable as potential anti-Alzheimer's drugs. Specific activators are preferable to compounds such as bryostatin that show less specificity because non-specific activation of PKCδ or β could produce undesirable side effects.

Moreover, PKCε is also expressed at very low levels in all normal tissues except for brain. Mischak et al., *J. Biol. Chem.* 1993; 268: 6090-6096; Van Kolen et al., *J. Neurochem.* 2008; 104:1-13. The high abundance of PKCε in presynaptic nerve fibers suggest a role in neurite outgrowth or neurotransmitter release. Shirai et al., *FEBS J*. 2008; 275: 3988-3994). Therefore, effects of specific PKCε activators would be largely restricted to brain, and unlikely to produce unwanted peripheral side effects.

PUFAs as PKC Activators

Some PUFAs, such as arachidonic acid (see FIG. 1), have been known for many years to be natural activators of PKC. Docosahexaenoic acid (DHA) is also a known activator of PKC and has recently been shown to slow the accumulation of Aβ and tau proteins associated with the brain-clogging plaques and tangles implicated in AD. Sahlin et al., *Eur J Neurosci*. 2007; 26(4):882-9.

Kanno et al. described effect of 8-[2-(2-pentyl-cyclopropylmethyl)-cyclopropyl]-octanoic acid (DCP-LA), a newly synthesized linoleic acid derivative with cyclopropane rings instead of cis-double bonds, on protein kinase C (PKC) activity. *Journal of Lipid Research*. 2007; 47: 1146-1156. DCP-LA activated PKCε, with a greater than 7-fold potency over other PKC isozymes. This indicates that DCP-LA is highly specific for PKCε. This compound also facilitated hippocampal synaptic transmission by enhancing activity of presynaptic acetylcholine receptors on the glutamatergic terminals or neurons. However, DCP-LA requires relatively high concentrations to produce its maximal effect.

WO 2002/50113 to Nishizaki et al., discloses carboxylic acid compounds and their corresponding salts having cyclopropane rings for LTP-like potentiation of synaptic transmission or for use as a cognition-enhancing drug or a drug to treat dementia. Their synthetic examples disclose preparation of esters but their experimental results teach the use of free acids. The reason is that the carboxylic acid group of the fatty acid starting material would react with the diethylzinc used in the Simmons-Smith reaction. The methyl ester acts as a protecting group and may be cleaved off by hydrolysis or allowed to remain as needed.

The caveats with the prior art finding include the necessity of administering high concentrations of to achieve the foregoing effects, non-specific activation of PKC isoforms, or rapid metabolism and sequestration of unmodified PUFAs into fat tissues and other organs where they are incorporated into triglycerides and chylomicrons. *J Pharmacobiodyn*. 1988; 11(4):251-61. In addition use of unmodified PUFAs would have a myriad of adverse side effects. For example, arachidonic acid is a biochemical precursor to prostaglandins, thromboxanes, and leukotrienes, which have potent pro-inflammatory effects. This would be undesirable for treatment of Alzheimer's disease where the pathology likely involves inflammation. Other essential fatty acids may also possess a multitude of other biological effects, including enhancement of nitric oxide signaling, anti-inflammatory effects, and inhibition of HMG-CoA reductase, which would interfere with cholesterol biosynthesis.

Because of the limited existing options for treating both AD and stroke, new therapeutics that can selectively activate only the PKC isoforms that elicit neuroprotection are needed.

PUFAs and MUFAs and Disease

A growing number of studies have suggested that omega-3 PUFAs can be beneficial for other mood disturbance disorders such as clinical depression, bipolar disorder, personality disorders, schizophrenia, and attention deficit disorders. Ross et al., *Lipids Health Dis.* 2007; 18; 6:21. There is an abundance of evidence linking omega-3 fatty acids, particularly docosahexaenoic and eicosapentaenoic acids, and a healthy balance of omega-3 to omega-6 fatty acids, to lowering the risk of depression. Logan et al., *Lipids Health Dis.* 2004; 3: 25. Levels of omega-3 fatty acids were found to be measurably low and the ratio of omega-6 to omega-3 fatty acids were particularly high in a clinical study of patients hospitalized for depression. A recent study demonstrated that there was a selective deficit in docosahexaenoic in the orbitofrontal cortex of patients with major depressive disorder. McNamara et al, *Biol Psychiatry.* 2007; 62(1):17-24. Several studies have also shown that subjects with bipolar disorder have lower levels omega-3 fatty acids. In several recent studies, omega-3 fatty acids were shown to be more effective than placebo for depression in both adults and children with bipolar depression. Osher and Belmaker, *CNS Neurosci Ther.* 2009; 15(2):128-33; Turnbull et al., *Arch Psychiatr Nurs.* 2008; 22(5): 305-11.

Extensive research also indicates that omega-3 fatty acids reduce inflammation and help prevent risk factors associated with chronic diseases such as heart disease, cancer, inflammatory bowel disease and rheumatoid arthritis. Calder et al., *Biofactors.* 2009; 35(3):266-72; Psota et al., *Am J Cardiol.* 2006; 98(4A):3i-18i; Wendel et al, *Anticancer Agents Med Chem.* 2009; 9(4):457-70.

Monounsaturated fatty acids also have been shown to be beneficial in disorders. There is good scientific support for MUFA diets as an alternative to low-fat diets for medical nutrition therapy in Type 2 diabetes. Ros, American *Journal of Clinical Nutrition.* 2003; 78(3): 617S-625S. High-monounsaturated fatty acid diets lower both plasma cholesterol and triacylglycerol concentrations. Kris-Etherton et al, *Am J Clin Nutr.* 1999 December; 70(6):1009-15.

Figure 1:
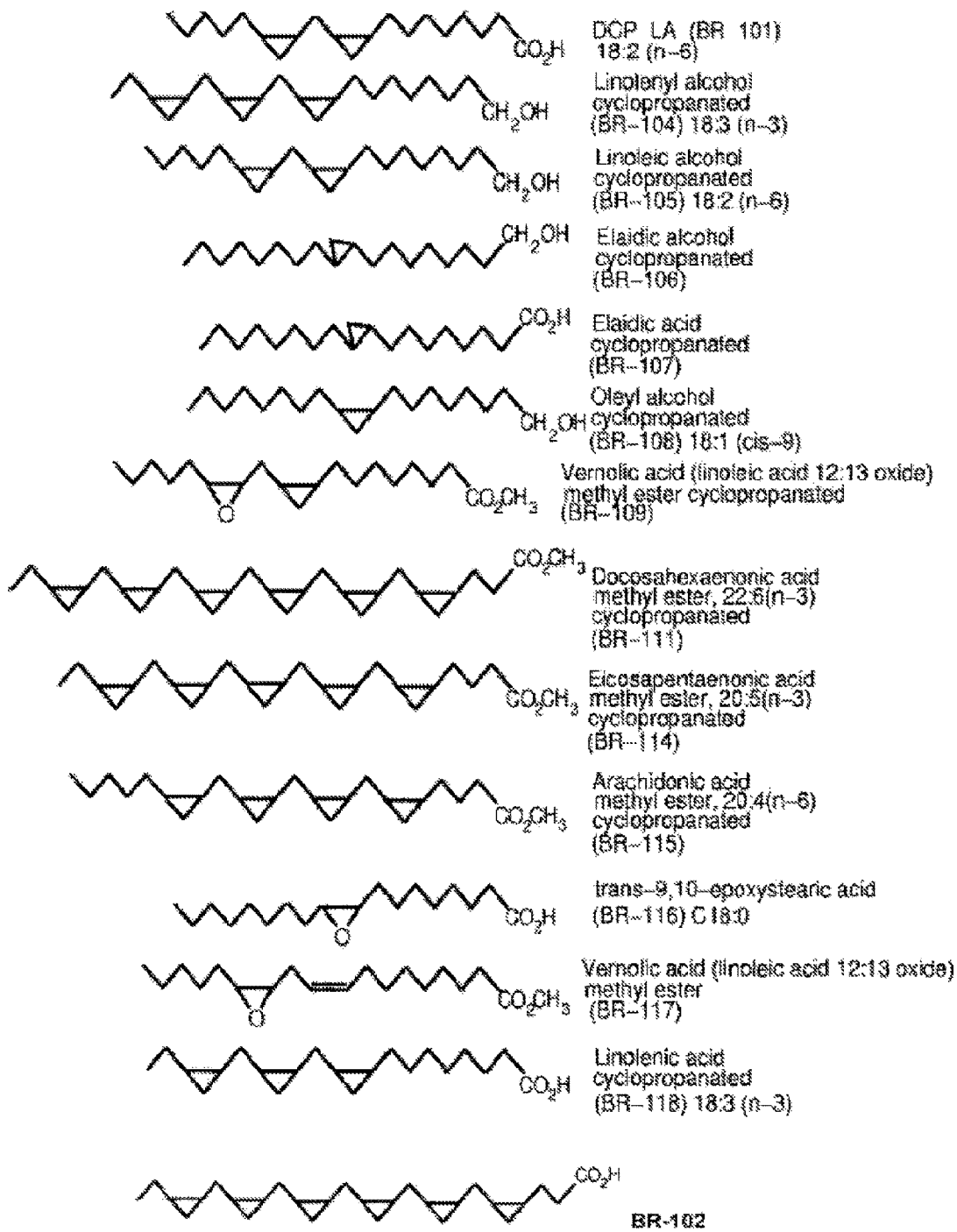
FIG. 1. Structures of and of molecules contemplated for use according to the present invention (BR-101 through BR-118).

The present invention provides a method for activating PKCε using certain derivatives of polyunsaturated fatty acids (PUFA) or monounsaturated fatty acids (MUFA). These compounds activate PKCε at nanomolar concentrations which makes them excellent candidates for the treatment of AD, stroke, and other neurological diseases in which PKCε is neuroprotective.

Definitions

A "fatty acid" is a carboxylic acid with an unbranched aliphatic chain containing from about 4 to 30 carbons; most long chain fatty acids contain between 10 and 24 carbons. Fatty acids can be saturated or unsaturated. Saturated fatty acids do not contain any double bonds or other functional groups along the chain. Unsaturated fatty acids contain one or more alkenyl functional groups, i.e., double bonds, along the chain. The term "polyunsaturated fatty acid" or "PUFA" means a fatty acid containing more than one double bond. There are three classes of PUFAs, omega-3 PUFAs, omega-6 PUFAs, and omega-9 PUFAS. In omega-3 PUFAs, the first double bond is found 3 carbons away from the last carbon in the chain (the omega carbon). In omega-6 PUFAs the first double bond is found 6 carbons away from the chain and in omega-9 PUFAs the first double bond is 9 carbons from the omega carbon.

PUFAs are also called "polyenoic fatty acids." As used herein, the term PUFA includes both naturally-occurring and synthetic fatty acids. A major source for PUFAs is from marine fish and vegetable oils derived from oil seed crops, although the PUFAs found in commercially developed plant oils are typically limited to linoleic acid and linolenic acid (18:3 delta 9,12,15).

A "cis-PUFA" is one in which the adjacent carbon atoms are on the same side of the double bond.

The abbreviation X:Y indicates an acyl group containing X carbon atoms and Y double bonds. For example, linoleic acid would be abbreviated 18:2.

A "methylene-interrupted polyene" refers to a PUFA having two or more cis double bonds separated from each other by a single methylene group.

A "non-methylene-interrupted polyene," or "polymethylene-interrupted fatty acid," refers to a PUFA having two or more cis double bonds separated by more than one methylene group.

A "monounsaturated fatty acid" (MUFA) is a fatty acid that has a single double bond in the fatty acid chain and all the remaining carbon atoms in the chain are single-bonded. Exemplary MUFAs include oleic acid, myristoleic acid and palmitoleic acid.

A "cis-monounsaturated fatty acid" means that adjacent hydrogen atoms are on the same side of the double bond.

Conjugated fatty acids such as conjugated linoleic acid (9-cis, 11-trans-octadecadienoic acid) possess a conjugated diene, that is, two double bonds on adjacent carbons. Some evidence suggests that conjugated linoleic acid has antitumor activity.

Exemplary PUFAs include lineoleic acid (9,12-octadecadienoic acid); γ-linolenic acid (GLA; 6,9,12-octadecatrienoic acid); α-linolenic acid (9,12,15-octadecatrienoic acid); arachidonic acid (5,8,11,14-eicosatetraenoic acid); eicosapentanoic acid (EPA; 5,8,11,14,17-eicosapentanoic acid); docosapentaenoic acid (DPA; 7,10,13,16,19-docosapentaenoic acid); docosahexaenoic acid (DHA; 4,7,10,13,16,19-docosahexanoic acid); and stearidonic acid (6,9,12,15-octadecatetraenoic acid).

As used herein, the term "cyclopropane" refers to a cycloalkane molecule with the molecular formula C3H6, consisting of three carbon atoms linked to each other to form a ring, with each carbon atom bearing two hydrogen atoms.

An "epoxide" refers to a cyclic ether with three ring atoms.

As used herein, a "PUFA derivative" refers to a PUFA, or alcohol or ester thereof, in which at least one of the double bonds has been cyclopropanated or epoxidized.

As used herein, a "MUFA derivative" refers to a MUFA, or alcohol or ester thereof, in which the double bond has been cyclopropanated or epoxidized.

Selective activation" of PKCε means that the PUFA derivative compound of the present invention activates PKCε to a greater detectable extent than any other PKC isozyme. In specific embodiments, the PUFA derivative activates PKCε at least 1-fold, 2-fold or 5-fold over the other PKC isozymes as measured using e.g., the PKC activation assay described herein. Upon activation, protein kinase C enzymes are translocated to the plasma membrane by RACK proteins (membrane-bound receptor for activated protein kinase C proteins). In general, upon activation, protein kinase C enzymes are translocated to the plasma membrane by RACK proteins. Other indicia of PKC activation include phosphorylation at specific C-terminal serine/threonine residues by phosphatidylinositol-trisphosphate-dependent kinase (PDK1), with at least two additional phosphorylations and/or autophosphorylations of well-conserved sequences in each enzyme of the PKC family. Activation of PKC is described in Sun and Alkon, *Recent Patents CNS Drag Discov.* 2006; 1(2): 147-56.

"Neurodegeneration" refers to the progressive loss of structure or function of neurons, including death of neurons.

For purposes of the present invention, a "neurological disease" refers to any central nervous system (CNS) or peripheral nervous system (PNS) disease that is associated with the β-amyloidogenic processing of APP. This may result in neuronal or glial cell defects including but not limited to neuronal loss, neuronal degeneration, neuronal demyelination, gliosis (i.e., astrogliosis), or neuronal or extraneuronal accumulation of aberrant proteins or toxins (e.g., Aβ).

One exemplary neurological disease is AD. Another exemplary neurological disease is congophilic angiopathy (CAA), also referred to as cerebral amyloid angiopathy.

The term "Alzheimer's Disease" or "AD" refers to any condition where Aβ deposition will eventually in the cells of the central nervous system. In one, non-limiting embodiment, Aβ, particularly Aβ1-42, peptide is formed from the β-amyloidogenic metabolism of APP. AD may be heritable in a Familial manifestation, or may be sporadic. Herein, AD includes Familial, Sporadic, as well as intermediates and subgroups thereof based on phenotypic manifestations.

Another neurological disease is Down syndrome (DS). Subjects with DS invariably develop (in their third or fourth decade) cerebral amyloid (Aβ) plaques and neurofibrillary tangles (NFTs), the characteristic lesions of AD. Recent studies have shown that the Aβ42 is the earliest form of this protein deposited in Down syndrome brains, and may be seen in subjects as young as 12 years of age, and that soluble Aβ can be detected in the brains of DS subjects as early as 21 gestational weeks of age, well preceding the formation of Aβ plaques. Gyure et al., *Archives of Pathology and Laboratory Medicine.* 2000; 125: 489-492.

As used herein, the term "subject" includes a mammal.

The phrase "pharmaceutically acceptable" refers to molecular entities and compositions that are physiologically tolerable and do not typically produce untoward reactions when administered to a subject. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans. The term "pharmaceutically acceptable carrier" means a chemical composition with which the active ingredient may be combined and which, following the combination, can be used to administer the active ingredient to a subject and can refer to a diluent, adjuvant, excipient, or vehicle with which the compound is administered.

The terms "therapeutically effective dose" and "effective amount" refer to an amount of a therapeutic agent that results in a measurable therapeutic response. A therapeutic response may be any response that a user (e.g., a clinician) will recognize as an effective response to the therapy, including improvement of symptoms and surrogate clinical markers. Thus, a therapeutic response will generally be an amelioration or inhibition of one or more symptoms of a disease or condition e.g., AD. A measurable therapeutic response also includes a finding that a symptom or disease is prevented or has a delayed onset, or is otherwise attenuated by the therapeutic agent.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The present invention includes use of cyclopropanated and epoxidized derivatives of PUFAs or MUFAs in which one, some, or all of the double bonds are replaced by a cyclopropane group or an epoxide group. The terminal function may be a free carboxylic acid, or a methyl ester, ethyl ester, or some other alkyl ester with an aliphatic or aromatic alcohol. This alcohol specifically may also include glycerol and derivatives thereof. Glycerol derivatives are biologically important because the fatty acids are most frequently found conjugated to glycerol in the form of phosphatidylcholine, phosphatidylserine, or phosphatidic acids. For example, triacylglycerols are compounds in which the carboxyl groups of fatty acids are esterified to the hydroxyls of all three carbons found in glycerol are referred to as triacylglycerols or triglycerides.

The purpose of esterifying the carboxylic acid is to facilitate transport across the blood-brain barrier by eliminating the negative charge. The purpose of an alcohol group is also to facilitate transport across the blood-brain bander.

In one embodiment, the fatty acid which forms the basis for the compounds used in the present invention is a polyunsaturated fatty acid having the following structure:

$$CH_3(CH_2)_4(CH=CHCH_2)x(CH_2)yCOOH$$

wherein X is between 2 and 6, and γ is between 2 and 6, and include methylene- or polymethylene-interrupted polyenes. Exemplary polyunsaturated fatty acids include linoleic acid, γ-linoleic, arachidonic acid, and adrenic acid having the following structures:

| | |
|---|---|
| $CH_3(CH_2)_4(CH=CHCH_2)_2(CH_2)_6COOH$ | Linoleic |
| $CH_3(CH_2)_4(CH=CHCH_2)_2(CH_2)_3COOH$ | γ-Linolenic |
| $CH_3(CH_2)_4(CH=CHCH_2)_2(CH_2)_2COOH$ | Arachidonic |
| $CH_3(CH_2)_4(CH=CHCH_2)_2(CH_2)_4COOH$ | Adrenic |

These are omega-6 PUFAs.

In another embodiment, the fatty acid which forms the basis for the compounds used in the present invention is a polyunsaturated fatty acid having the following structure:

$$CH_3CH_2(CH=CHCH_2)x(CH_2)yCOOH$$

wherein X is between 2 and 6, and γ is between 2 and 6 and include methylene- or polymethylene-interrupted polyenes. Exemplary polyunsaturated fatty acids include α-lineoleic acid, docosahexaenoic acid, eicosapentaenoic acid, eicosatetraenoic acid having the following structures:

| | |
|---|---|
| $CH_3CH_2(CH=CHCH_2)_3(CH_2)_6COOH$ | Alpha-Linolenic |
| $CH_3CH_2(CH=CHCH_2)_4(CH_2)_5COOH$ | Eicosatetraenoic |
| $CH_3CH_2(CH=CHCH_2)_5(CH_2)_2COOH$ | Eicosapentaenoic |
| $CH_3CH_2(CH=CHCH_2)_6(CH_2)_2COOH$ | Docosahexaenoic |

These are known as omega-3 PUFAs.

In a specific embodiment, the compound of the present invention is an ester of a cis-PUFA, in which the hydroxyl group is replaced by an alkoxy group, and in which at least one of the double bonds has been cyclopropanated. The starting material for this embodiment has the following structures:

$$CH_3(CH_2)_4(CH=CHCH_2)x(CH_2)yCOOR \text{ or}$$
$$CH_3CH_2(CH=CHCH_2)x(CH_2)yCOOR$$

wherein R is the alkyl group from an alcohol including monohydric alcohols and polyhydric alcohols including but not limited to methanol, ethanol, propanol, butanol, pentanol, glycerol, mannitol, and sorbitol.

In a further embodiment, the compound contains at least three cyclopropanated double bonds.

In another embodiment, the fatty acid which forms the basis for the compounds used in the present invention is a monounsaturated fatty acid having the following structure:

$$CH_3(CH_2)xCH=CH(CH_2)yCOOH$$

wherein X and Y are odd numbers between 3 and 11.

Exemplary mono unsaturated fatty acids that can be the basis for the compounds used in the present invention include cis- and trans-monounsaturated fatty acids such as oleic acid, elaidic acid, obtusilic acid, caproleic acid, lauroleic acid, linderic acid, myristoleic acid, palmitoleic acid, vaccenic acid, gadoleic acid, erucic acid, and petroselinic acid.

An ester according to the invention, means a monoester or a polyester. Esters of fatty acids include methyl, propyl, and butyl esters, and also esters resulting from more complex alcohols such as propylene glycol. In non-limiting embodiments, R' is straight or branched and includes methyl, ethyl, propyl, isopropyl, butyl, isobutyl, secbutyl, tert-butyl, pentyl, hexyl, heptyl, octyl, nonyl, decyl, undecyl, dodecyl, tridecyl, and tetradecyl. An ester may also be formed from a fatty acid linked to a fatty alcohol in an ester linkage.

The ester can be a alcohol ester, including but not limited to an aliphatic alcohol ester. In one embodiment, the alcohol ester is a glycerol ester. Glycerol esters of fatty acids include glycerol fatty acid ester, glycerol acetic acid fatty acid ester, glycerol lactic acid fatty acid ester, glycerol citric acid fatty acid ester, glycerol succinic acid fatty acid ester, glycerol diacetyl tartaric acid fatty acid ester, glycerol acetic acid ester, polyglycerol fatty acid ester, and polyglycerol condensed ricinoleic acid ester.

In another specific embodiment, the compound is an alcohol of a cis-PUFA in which at least one of the double bonds has been cyclopropanated. In a further embodiment, the compound is an alcohol of a cis-PUFA which contains at least three cyclopropanated double bonds. These compounds include but are not limited to linoleic alcohol dicyclopropane (BR-105), or linolenic alcohol tricyclopropane (BR-104). In this embodiment, R' can be a normal or branched chain alcohol or a phenolic alcohol.

In another embodiment, the compound of the present invention, the compound is a cis-polyunsaturated fatty acid, or derivative thereof, in which at least one of the double bonds is replaced with an epoxyl group. In a further embodiment, the compound contains at least three epoxidized double bonds.

In a specific embodiment, the compound is an epoxidized ester of a cis-PUFA, including but not limited to a fatty alcohol ester. The esters can be the same esters as described above for the cyclopropanated PUFAS. In a further embodiment the alcohol can be an aliphatic alcohol ester, such as glycerol.

In another specific embodiment, the compound is an epoxidized cis-polyunsaturated fatty alcohol such as linoleic alcohol dicyclopropane or linolenic alcohol tricyclopropane. The alcohols can be the same as described above for the cyclopropanated PUFAS.

In another embodiment, the compound includes cyclopropanated or epoxidized lipids derived from cis-monounsaturated fatty acids (cis-monoenoic acids), such as oleic acid, elaidic acid, elaidic alcohol, oleyl alcohol, and 1-monolinoleyl rac-glycerol. Exemplary compounds include eliadic alcohol cyclopropane (BR-106), eliadic acid cyclopropane (BR-107), and oleyl alcohol cyclopropane (BR-108).

A further embodiment includes cyclopropanated lipids derived from cis-monounsaturated fatty acids or unsaturated fatty acids, fatty acid esters, or fatty acid alcohols, containing one or more epoxide residues, such as vernolic acid methyl ester cyclopropane (e.g., BR-109).

In specific embodiments, the PUFAs which forms the basis of the cyclopropanated compounds used in the present invention include but are not limited to arachidonic acid (AA), docosahexaenoic acid (DFIA), and eicosapentaenoic acid (EPA). Exemplary compounds for use in the method of the present invention include docahexaenonic acid methyl ester hexacyclopropane (BR-111); eicosapentaenoic acid methyl ester pentacyclopropane (BR-114); and arachidonic acid methyl ester tetracyclopropane (BR-115).

In a further specific embodiment, the compound is a cyclopropanated PUFA derivative of docosahexaenoic acid having the following structure:

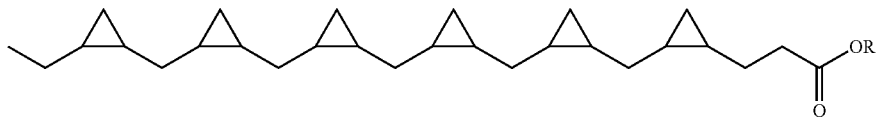

in which R is H or an alkyl group. In a specific embodiment, R is CH3 (BR-111 or DHA-CB6 methyl ester or methyl-3-(2-((2-((2-((2-((2-((2-ethylcyclopropyl)methyl)cyclopropyl)methyl)cyclopropyl)methyl)-cyclopropyl)methyl)cyclopropyl)methyl)cyclopropyl)propanoate.

In another specific embodiment, the PUFA derivative has the following structure:

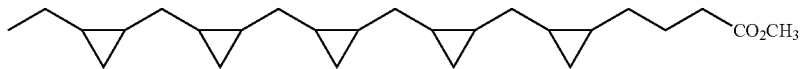

This compound is BR-114 (EPA-CP5 or methyl 4-(2((2-((2-((2-ethylcyclopropyl)methyl)cyclopropyl)methyl)cyclopropyl)methyl)cyclopropyl)methyl)-cyclopropyl)butanoate methyl ester).

In still another specific embodiment, the PUFA derivative has the following structure:

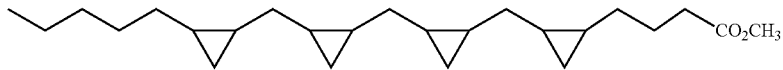

This compound is BR-115 (AA-CP4 or methyl 4-(2-((2-((2-((-pentylcyclopropyl)methyl)cyclopropyl)methyl)cyclopropyl)methyl)cyclopropyl)butanoate methyl ester).

In yet another specific embodiment, the PUFA derivative has the following structure:

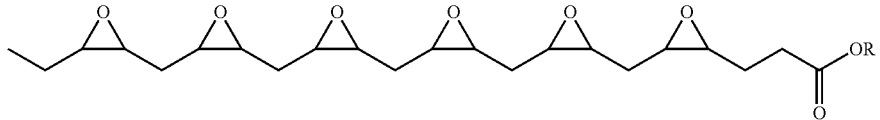

in which R is II or an alkyl ester. In a specific embodiment, R is CII3.

Naturally cyclopropanated or epoxidized MUFAS or ester or alcohol derivatives thereof contemplated for use in the present invention include malvenic acid, vernolic acid, and sterculic acid. An exemplary compound is vernolic acid methyl ester (BR-117).

Methods of Synthesis

Fatty acids, and esters and alcohols thereof, can be obtained or made from purification from natural sources, e.g., fish oil, flaxseed oil, soybeans, rapeseed oil, or algae, or synthesized using a combination of microbial enzymatic synthesis and chemical synthesis. As one example, fatty acid methyl esters can be produced by the transesterification of triglycerides of refined/edible type oils using methanol and an homogeneous alkaline catalyst.

Methods of cyclopropanation of double bonds in hydrocarbons are well known. As one example, the modified Simmons-Smith reaction is a standard method for converting double bonds to cyclopropanes. Tanaka and Nishizaki, *Bioorg. Med. Chem. Let.* 2003; 13: 1037-1040; Kawabata and Nishimura, J. *Tetrahedron.* 1967; 24: 53-58; and Denmark and Edwards, *J. Org Chem.* 1991; 56: 6974. In this reaction, treatment of alkenes with metal carbenoids, e.g., methylene iodide and diethylzinc, result in cyclopropanation of the alkene. See also, Ito et al., *Organic Syntheses.* 1988; 6:327. Cyclopropanation of methyl esters of was also effected using diazomethane in the presence of palladium (II) acetate as catalyst. Gangadhar et al., *Journal of the American Oil Chemists' Society.* 1988; 65(4): 601-606.

Methods of epoxidation are also well known and typically involve reaction of fatty acids dioxiranes in organic solvents. Sonnet et al., *Journal of the American Oil Chemists' Society.* 1995; 72(2): 199-204. As one example, epoxidation of PUFA double bonds can be achieved using dimethyldioxirane (DMD) as the epoxidizing agent. Grabovskiy et al., *Helvetica Chimica Acta.* 2006; 89(10): 2243-53.

Methods of Treatment

The present invention contemplates treatment of neurological diseases associated with pathogenic Aβ such as AD and stroke using the PUFA derivatives disclosed herein. The present invention also contemplates prevention of neurological diseases associated with pathogenic Aβ using the PUFA derivatives disclosed herein. Without being limited to any particular mechanism, selective activation of PKCε may result in increased activation of TACE, with a concomitant decrease in production of Aβ. However, this appears to occur mainly in non-neuronal cells such as fibroblasts. Activation of PKCε may also reduce the hyperphosphorylation of the pathogenic tau protein in AD. Activation of PKCε may also induce synaptogenesis or prevent apoptosis in AD or following stroke. Activation of PKCε may also protect rat neurons from Aβ-mediated neurotoxicity through inhibition of GSK-3β. PKCε activators may also counteract the effect of Aβ on the downregulation of PKC α/ε, and thereby reverse or prevent the Aβ-induced changes. Another possible mechanism of action is the activation of Aβ-degrading enzymes such as endothelin-converting enzyme. The results of experiments presented in the Examples suggest that this may be the mechanism of action.

Yet another mechanism may be by stimulation of PKC-coupled M1 and M3 muscarinic receptors, which is reported to increase nonamyloidogenic APP processing by TACE. Rossner et al., *Prog. Neurobiol.* 1998; 56: 541-569. Muscarinic agonists rescue 3x-transgenic AD mice from cognitive deficits and reduce Aβ and tau pathologies, in part by activating the TACE/ADAM17 nonamyloidogenic pathway. Caccamo et al., *Neuron.* 2006; 49:671-682. Muscarinic receptor signaling is closely tied to PKC. Muscarinic receptor mRNA is regulated by PKC and neuronal differentiation produced by M1 muscarinic receptor activation is mediated by PKC. Barnes et al., *Life Sci.* 1997; 60:1015-1021; Vandemark et al., *J. Pharmacol. Exp. Ther.* 2009; 329(2): 532-42.

Other disorders contemplated for treatment by the methods of the present invention include, mood disorders such as depressive disorders and bipolar disorder, schizophrenia, rheumatoid arthritis, cancer, cardiovascular disease, type 2 diabetes, and any other disorder in which PUFAs or MUFAs have been shown to be beneficial, including but not limited to those mention in the background.

Formulation and Administration

The PUFA derivatives may be produced in useful dosage units for administration by any route that will permit them to cross the blood-brain barrier. It has been demonstrated PUFAs from plasma are able to cross into the brain. Rapoport et al., *J. Lipid Res.* 2001. 42: 678-685. Exemplary routes include oral, parenteral, transmucosal, intranasal, inhalation, or transdermal routes. Parenteral routes include intravenous, intra-arteriolar, intramuscular, intradermal, subcutaneous, intraperitoneal, intraventricular, intrathecal, and intracranial administration.

The compounds of the present invention can be formulated according to conventional methods. The PUFA derivative compounds can be provided to a subject in standard formulations, and may include any pharmaceutically acceptable additives, such as excipients, lubricants, diluents, flavorants, colorants, buffers, and disintegrants. Standard formulations are well known in the art. See e.g., Remington's Pharmaceutical Sciences, 20th edition, Mack Publishing Company, 2000.

In one embodiment, the compound is formulated in a solid oral dosage form. For oral administration, e.g., for PUFA, the pharmaceutical composition may take the form of a tablet or capsule prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

As one example, the drug Omacor® contains concentrated combinations of ethyl esters of an omega-3 PUFAS. Each 1-g capsule contains at least 900 mg of the ethyl esters of omega-3 fatty acids, primarily EPA (465 mg) and DHA (375 mg), according to the drug's label. Omacor® is administered up to 4 times per day as 1-gram transparent soft gelatin capsules filled with light-yellow oil. A similar composition can be used to administer the PUFA compounds of the present invention, although the present invention contemplates use of a lower dose of the PUFA derivatives. Stable wax-ester formulations of PUFAs have also been described by transesterification of stoichiometric amounts of ethyl esters enriched with n-3 PUFA and long-chain alcohols (18-22 carbon atoms) by transesterification of stoichiometric amounts of ethyl esters enriched with n-3 PUFA and long-chain alcohols (18-22 carbon atoms). Goretta et al., *Lebensmittel-Wissenschaft und-Technologie.* 2002; 35(5): 458-65.

In another embodiment, the PUFA compound is formulated for parenteral administration. The compound may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, dispersions, or emulsions in oily or aqueous vehicles, and may contain formulatory agents such as suspending, stabilizing and/or dispersing agents.

In a specific embodiment, the PUFA derivatives of the present invention are administered with a hydrophobic carrier. Hydrophobic carriers include inclusion complexes, dispersions (such as micelles, microemulsions, and emulsions), and liposomes. Exemplary hydrophobic carriers are inclusion complexes, micelles, and liposomes. These formulations are known in the art (Remington's: The Science and Practice of Pharmacy 20th ed., ed. Gennaro, Lippincott: Philadelphia, Pa. 2003). The PUFA derivatives of the present invention may be incorporated into hydrophobic carriers, for example as at least 1, 5, 10, 20, 30, 40, 50, 60, 70, 80, or 90% of the total carrier by weight. In addition, other compounds may be included either in the hydrophobic carrier or the solution, e.g., to stabilize the formulation.

In addition to the formulations described previously, the PUFA derivative may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In another embodiment, the PUFA derivative can be delivered in a vesicle, particularly a micelle, liposome or an artificial LDL particle as described in U.S. patent application Ser. No. 11/648,808 to Alkon et al.

The doses for administration may suitably be prepared so as to deliver from 1 mg to 10 g, preferably from 10 mg to 1 g and very preferably from 250 mg to 500 mg of the compound per day. When prepared for topical administration or parenteral formulations they may be made in formulae containing from 0.01% to 60% by weight of the final formulation, preferably from 0.1% to 30% by weight, and very preferably from 1% to 10% by weight. The optimal daily dose will be determined by methods known in the art and will be influenced by factors such as the age of the patient and other clinically relevant factors.

Combination Drug Therapy

The PUFA compound can be used to treat patients with AD or other neurological disorders associated with A$\beta$ in combination with other drugs that are also used to treat the disorder. Exemplary non-limiting pharmacological agents approved in the United States for the treatment of AD include cholinesterase inhibitors such as Aricept® (donepezil), Exelon® (rivastigmine), Reminyl® (galantamine), and NMDA receptor antagonists such as Namenda® (memantine). Other potential therapeutic agents include protease inhibitors (see e.g., U.S. Pat. Nos. 5,863,902; 5,872,101; inhibitors of A$\beta$ production such as described in U.S. Pat. Nos. 7,011,901; 6,495,540; 6,610,734; 6,632,812; 6,713, 476; and 6,737,420; modulators of A$\beta$ aggregation, described in U.S. Pat. Nos. 6,303,567; 6,689,752; and inhibitors of BACE such as disclosed in U.S. Pat. Nos. 6,982,264; 7,034,182; 7,030,239. Exemplary drugs used for the treatment of stroke include aspirin, anti-platelet medications such as tissue plasminogen activator or other anticoagulants.

In a particular embodiment, the present invention contemplates combination therapy with other PKC activators, including but not limited to benzolactam macrocyclic lactones. Bryostatin-1 is a macrocyclic lactone that has been shown to modulate PKC and result in an increase in cleavage of APP by TACE into the non-amyloidogenic pathway. Bryostatin was able to increase the duration of memory retention of the marine slug *Hermissenda crassicornis* by over 500%, and was able to dramatically increase the rate of learning in rats. See U.S. patent application Ser. No. 10/919, 110; Kurzirian et al., *Biological Bulletin*. 2006; 210(3): 201-14; Sun and Alkon, *European Journal of Pharmacology*. 2005; 512(1): 43-51. Other non-limiting PKC activators are described in pending U.S. patent application Ser. No. 12/068,742 to Alkon et al.

Combinations with drugs that indirectly increase TACE, such as by inhibiting endogenous TACE inhibitors or by increasing endogenous TACE activators. An alternative approach to activating PKC directly is to increase the levels of the endogenous activator, diacylglycerol. Diacylglycerol kinase inhibitors such as 6-(2-(4-[(4-fluorophenyl)phenyl-methylene]-1-piperidinyl)ethyl)-7-methyl-5H-thiazolo[3,2-a]pyrimidin-S-one (R59022) and [3-[2-[4-(bis-(4-fluorophenyl)methylene]piperidin-1-yl)ethyl]-2,3-dihydro-2-thioxo-4 (1H)-quinazolinone (R59949) enhance the levels of the endogenous ligand diacylglycerol, thereby producing activation of PKC. Meinhardt et al. (2002) *Anti-Cancer Drugs* 13: 725.

Still another embodiment is combination therapy with BACE inhibitors. BACE inhibitors are known and include CTS-21166, owned by CoMentis Inc., which has shown positive results in a human clinical trial. Other BACE inhibitors are described in published International PCT application WO2007/019080 and in Baxter et al., *Med. Chem*. 2007; 50(18): 4261-4264.

Compounds used in combination therapy can be administered in the same formulation as the PUFA compound of the present invention, where compatible, or can be administered in separate formulations.

Evaluation of Treatment

Evaluation of treatment with the PUFA derivatives of the present invention can be made by evaluation improvement in symptoms or clinical surrogate markers of the disease. For example, improvement in memory or cognitive skills in a treated AD subject may suggest that there is a reduction of pathogenic A$\beta$ accumulation. Examples of cognitive phenotypes include, but are not limited to, amnesia, aphasia, apraxia and agnosia. Examples of psychiatric symptoms include, but are not limited to, personality changes, depression, hallucinations and delusions. As one non-limiting example, the Diagnostic and Statistical Manual of Mental disorders, 4th Edition (DSM-IV-TR) (published by the American Psychiatric Association) contains criteria for dementia of the Alzheimer's type.

Phenotypic manifestations of AD may also be physical, such as by the direct (imaging) or indirect (biochemical) detection of A$\beta$ plaques. In vivo imaging of A$\beta$ can be achieved using radioiodinated flavone derivatives as imaging agents (Ono et al., *J Med Chem*. 2005; 48(23):7253-60) and with amyloid binding dyes such as putrescine conjugated to a 40-residue radioiodinated A peptide (yielding 1251-PUT-A 1-40), which was shown to cross the blood-brain barrier and bind to A$\beta$ plaques. Wengenack et al., *Nature Biotechnology*. 2000; 18(8): 868-72. Imaging of A$\beta$ also was shown using stilbene[11C]SB-13 and the benzothiazole [11C]6-OH-BTA-1 (also known as [11C]PIB). Verhoeff et al., *Am J Geriatr Psychiatry*. 2004; 12:584-595.

Quantitation of A$\beta$ (1-40) in the peripheral blood has been demonstrated using high-performance liquid chromatography coupled with tandem mass spectrometry in a linear ion trap. Du et al., *J Biomol Tech*. 2005; 16(4):356-63. Detection of single A$\beta$ protein aggregates in the cerebrospinal fluid of Alzheimer's patients by fluorescence correlation spectroscopy also has been described. Pitschke et al., *Nature Medicine*. 1998; 4: 832-834. U.S. Pat. No. 5,593,846 describes a method for detecting soluble A$\beta$. Indirect detection of A$\beta$ peptide and receptor for advanced glycation end products (RAGE) using antibodies also has been described. Lastly, biochemical detection of increased BACE-1 activity in cerebrospinal fluid using chromogenic substrates also has been postulated as diagnostic or prognostic indicator of AD. Verheijen et al., *Clin Chem*. 2006; 52:1 168-11 74.

Current measures for evaluation AD include observation of a clinical core of early, progressive and significant episodic memory loss plus one or more abnormal biomarkers (biological indicators) characteristic of AD, including atrophy (wasting) of the temporal lobe as shown on MRI; abnormal A$\beta$ protein concentrations in the cerebrospinal fluid; a specific pattern showing reduced glucose metabolism on PET scans of the brain; and a genetic mutation associated with within the immediate family.

EXAMPLES

Example 1: Synthesis of Fatty Acid Methyl Esters Cyclopropanated Fatty Acid Methyl Esters Synthesis of Cyclopropanated Fatty Acids.

Methyl esters of polyunsaturated fatty acids were cyclopropanated using the modified Simmons-Smith reaction using chloroiodomethane and diethylzinc (Tanaka et al., *Bioorg. Med. Chem. Let*, 2003; 13: 1037-40; Furukawa et al., *Tetrahedron.* 1967; 53-58; Denmark et al., *J. Org. Chem.* 1991; 56: 6974-81). All apparatus was baked at 60° C. for 1 hr and dried using a flame with dry nitrogen. A 100 ml 3-neck round bottom flask with a stirring bar and a temperature probe was surrounded by an ice-dry ice mixture and filled with 1.25 g (4.24 mmol) linoleic acid methyl ester or docosahexaenoic acid methyl ester in 25 ml dichloromethane and bubbled with $N_2$. A 1M solution of diethylzinc (51 ml, 54.94 mmol) in hexane was added anaerobically using a 24-inch-long 20-gauge needle and the solution was cooled to −5° C. Diiodomethane (8.2 ml, 101.88 mmol) or chloroiodomethane (C1CH2 I) was added dropwise, one drop per second, with constant stirring. The rate of addition was decreased if necessary to maintain the reaction mixture below 2° C. The reaction mixture became cloudy during the reaction and an insoluble white zinc product was liberated. The flask was sealed and the mixture was allowed to react for 1 hr and then allowed to come to room temperature gradually over 2 hr.

To prevent the formation of an explosive residue in the hood, diethylzinc was not evaporated off. The mixture was slowly poured into 100 ml of water under stirring to decompose any excess diethylzinc. Ethane was evolved. The mixture was centrifuged at 5000 rpm in glass centrifuge tubes and the upper aqueous layer discarded. The white precipitate was extracted with $CH_2Cl_2$ and combined with the organic phase. The organic phase was washed with water and centrifuged. The product was analyzed by silica gel G TLC using hexane plus 1% ethyl acetate and purified by chromatography on silica gel using increasing concentrations of 1-10% ethyl acetate in n-hexane and evaporated under nitrogen, leaving the methyl ester as a colorless oil.

The Simmons-Smith reaction preserves the stereochemistry of the starting materials. Furukawa et al., *Tetrahedron.* 1967; 53-58. Docosahexaenoic acid methyl ester was converted into DHA-CP6 in 90-95% yield. The product was a colorless oil with a single absorbance maximum at 202 nm in ethanol and no reaction with $I_2$. The IR spectrum showed cyclopropane ring absorption at 3070 and 1450 $cm^{-1}$. Under the same conditions, eicosapentaenoic acid methyl ester was converted to EPA-CP5, and arachidonic acid methyl ester was converted to AA-CP4. Linoieic acid methyl ester was converted to DCP-LA methyl ester which was identical to a known sample.

Hydrolysis of Methyl Ester.

The methyl ester (0.15 g) was dissolved in 1 ml 1N LiOH and 1 ml dioxane. Dioxane and methanol were added until it became homogeneous and the solution was stirred 60° overnight. The product was extracted in CH2Cl2 and centrifuged. The aqueous layer and white interface were re-extracted with water and washed until the white layer no longer formed. The product was evaporated under $N_2$ and purified by chromatography on silica gel. The product, a colorless oil, eluted in 20% EtOAc in n-hexane. Its purity was checked by TLC in 10% EtOAc/hexane and by C18 RP-HPLC using UV detection at 205 nm.

The epoxide groups can be introduced by conventional means, e.g., by oxidation of the appropriate alkene with m-chloroperbenzoic acid or t-butylhydroperoxide.

Other compounds synthesized include those depicted in FIG. 1 (BR-101 through BR-118).

Example 2: Activation of Purified PKC Epsilon Using Docosahaexanoic Acid

Protein Kinase C Assay.

Recombinant PKC (1 ng of alpha or epsilon isoform) was mixed with the BR-101 (DCP-LA) in the presence of 10 micromoiar histones, 5 mM $CaCl_2$, 1.2 µg/µl phosphatidyl-L-serine, 0.18 µg/µl 1,2-dioctanoyl-sn-glycerol (DAG), 10 mM $MgCL_2$, 20 mM HEPES (pH 7.4), 0.8 mM EDTA, 4 mM EGTA, 4% glycerol, 8 µg/ml aprotinin, 8 µg/ml leupeptin, and 2 mM benzamidine. 0.5 micro Ci [$γ^{32}P$]ATP was added. The incubation mixture was incubated for 15 min at 37 degrees in a total volume of 10 microliters. The reaction was stopped by spotting the reaction mixtures on 1×2 cm strips of cellulose phosphate paper (Whatman P81) and immediately washing twice for 1 hr in 0.5% $H_3PO_4$. The cellulose phosphate strips were counted in a scintillation counter. In some experiments, phosphatidylserine, diacylglycerol, and/or calcium were removed.

DHA methyl ester was purchased from Cayman Chemical (Ann Arbor, Me.). PKC isozymes were from Calbiochem (San Diego, Calif.). Purified PKCε was purchased from Calbiochem.

Results

Figure 2:
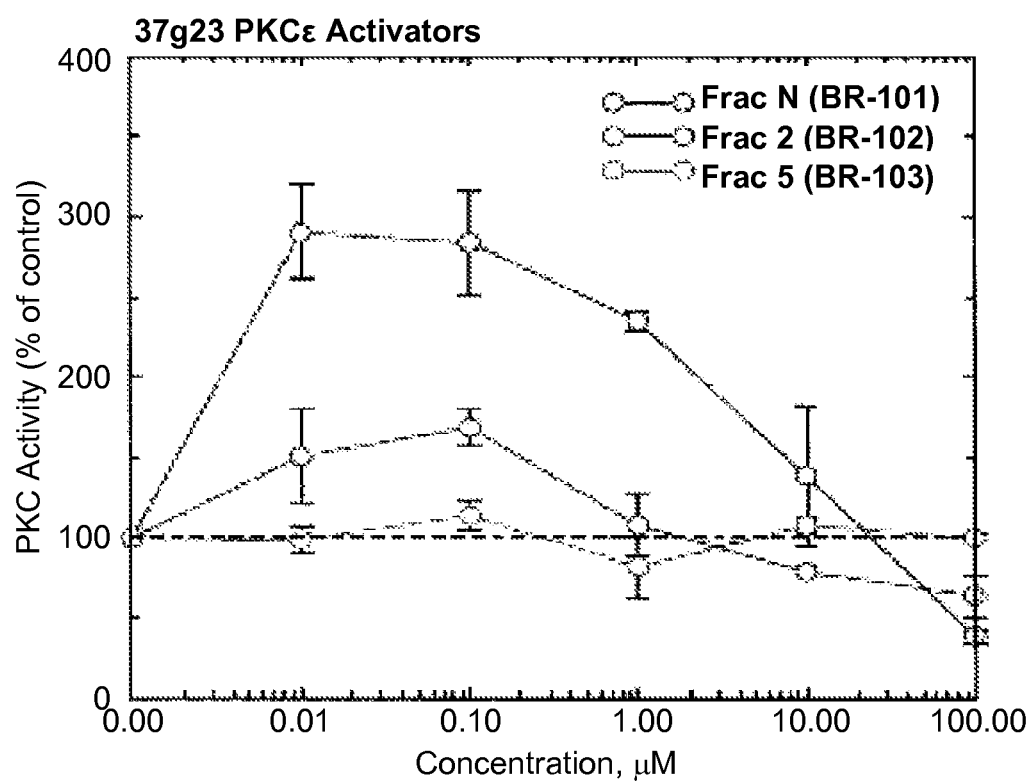
FIG. 2 shows the results of an in vitro PKCε activation by BR-101 (DCP-LA) and two less active derivatives, BR-102 and BR-103.

PKC measurements using purified PKCε showed that, at the lowest concentration tested (10 nM), compound BR-101 produced a 2.75-fold activation of PKCε (FIG. 2). PKCα was not affected (data not shown). Compound BR-102 also selectively elicited activation of PKCε to about 1.75 fold over unactivated PKCε. The effectiveness of these compounds in activating PKCε at low concentrations suggests that they will be good therapeutic candidates.

Example 3: Activation of Purified or Cellular PKC Epsilon Using Other PKC Activators Materials.

Culture media were obtained from K-D Medical (Columbia, Md.) or Invitrogen (Carlsbad, Calif.). Aβ1-42 was purchased from Anaspec (San Jose, Calif.). Polyunsaturated fatty acid methyl esters were obtained from Cayman Chemicals, Ann Arbor, Mich. Other chemicals were obtained from Sigma-Aldrich Chemical Co. (St. Louis, Mo.). PKC isozymes were from Calbiochem (San Diego, Calif.). Purified PKCε was purchased from Calbiochem.

Cell Culture.

Rat hippocampal H19-7/IGF-IR cells (ATCC, Manassas, Va.) were plated onto poly-L-lysine coated plates and grown at 35° C. in DMEM/10% FCS for several days until about 50% coverage was obtained. The cells were then induced to differentiate into a neuronal phenotype by replacing the medium with 5 ml $N_2$ medium containing 10 ng/ml basic fibroblast growth factor at 39° C. and grown in T-75 flasks at 37° C. Human SH-SY5Y neuroblastoma cells (ATCC) were cultured in 45% F12K/45% MEM/10% FCS. Mouse N2A neuroblastoma cells were cultured in DMEM/10% FCS without glutamine. Rat hippocampal neurons from 18-day-old embryonic Sprague Dawley rat brains were plated on 12- or 96-well plates coated with poly-D-lysine (Sigma-Aldrich, St, Louis, Mo.) in B-27 neurobasal medium containing 0.5 mM glutamine and 25 uM glutamate (Invitrogen, Carlsbad, Calif.) and cultured for three days in the medium without glutamate. The neuronal cells were grown under 5% $CO_2$ in an incubator maintained at 37° C. for 14 days.

All experiments on cultured cells were carried out in triplicate unless otherwise stated. All data points are displayed as mean±SE. BR-101 (DCP-LA) was used as its free acid in all experiments, while BR-111 (DHA-CP6), BR-114 (EPA-CP5), and BR-116 (AA-CP4) were used as their methyl esters.

Protein Kinase C Assay.

Rat hippocampal cells were cultured and scraped in 0.2 ml homogenization buffer (20 mM Tris-HCl, pH 7.4, 50 mM NaF, 1 µg/ml leupeptin, and 0.1 mM PMSF) and homogenized by sonication in a Marsonix micro-probe sonicator (5 sec, 10 W). To measure PKC, 10 µl of cell homogenate or purified PKC isozyme (purchased from Calbiochem) was incubated for 15 min at 37° C. in the presence of 10 µM histones, 4.89 mM $CaCl_2$, 1.2 µg/µl phosphatidyl-L-serine, 0.18 µg/µl 1,2-dioctanoyl-sn-glycerol, 10 mM $MgCl_2$, 20 mM HEPES (pH 7.4), 0.8 mM EDTA, 4 mM EGTA, 4% glycerol, 8 µg/ml aprotinin, 8 µg/ml leupeptin, and 2 mM benzamidine. 0.5 µCi [$\gamma$-$^{32}$P]ATP was added and $^{32}$P-phosphoprotein formation was measured by adsorption onto phosphocellulose as described previously. Nelson and Alkon, *J. Neurochemistry.* 1995; 65: 2350-57. For measurements of activation by BR-101 (DCP-LA) and similar compounds, PKC activity was measured in the absence of diacylglycerol and phosphatidyl serine, as described by Kanno et al., and PKC δ, ε, η, and µ were measured in the absence of added EGTA and CaCl2, as described by Kanno et al., *J. Lipid Res.* 2006; 47: 1146-50. Low concentrations of $Ca^{2+}$ are used because high $Ca^{2+}$ interacts with the PKC phosphatidylserine binding site and prevents activation. For measurements of bryostatin activation, 1,2-diacylglycerol was omitted unless otherwise stated.

Results and Discussion

To determine their PKC isozyme specificity, the new compounds were preincubated with purified PKC for five minutes and the PKC activity was measured radiometrically. As shown for Example, 2, above, BR-101 (DCP-LA) was an effective activator of PKCε at 10 µM but had relatively small effects on the other PKC isoforms (data not shown). At higher concentrations BR-101 (DCP-LA) partially inhibited PKCδ (about 1-100 µM) and activated PKCγ (50-100 µM) (data not shown).

Figure 3:
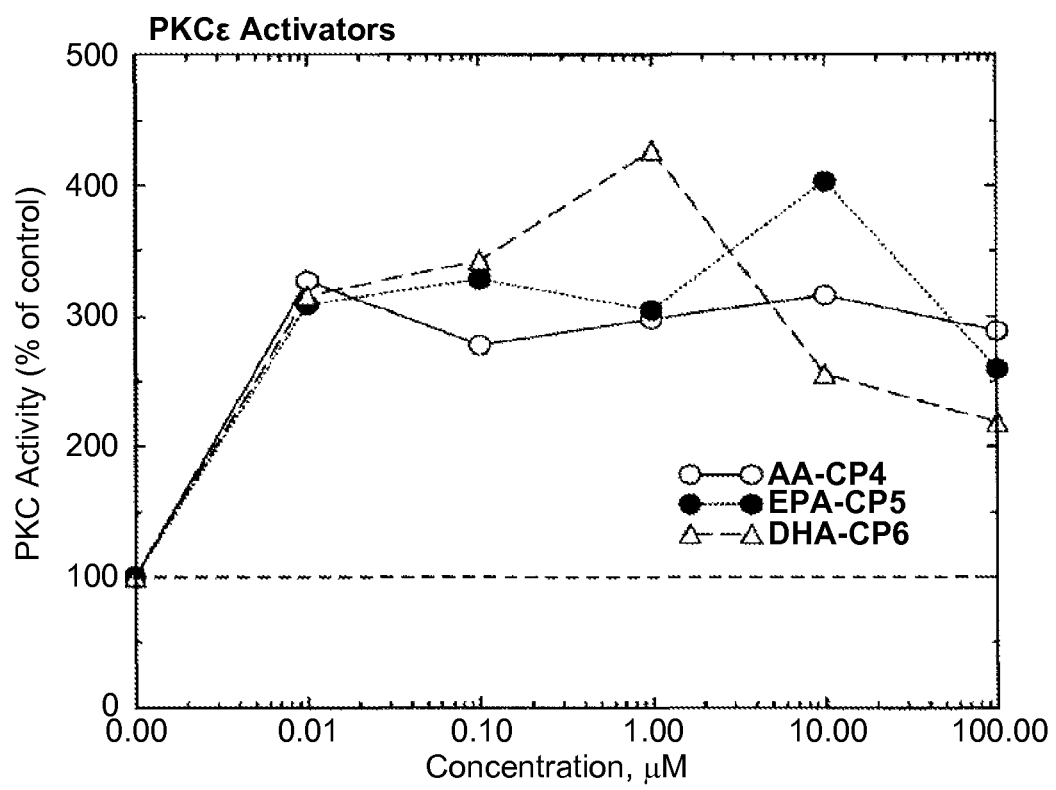
FIG. 3 shows activation of PKCε with various concentrations of BR-111 (DHA-CP6 methyl ester); BR-114 (EPA-CP5 methyl ester); and BR-115 (AA-CP4 methyl ester).
Figure 4:
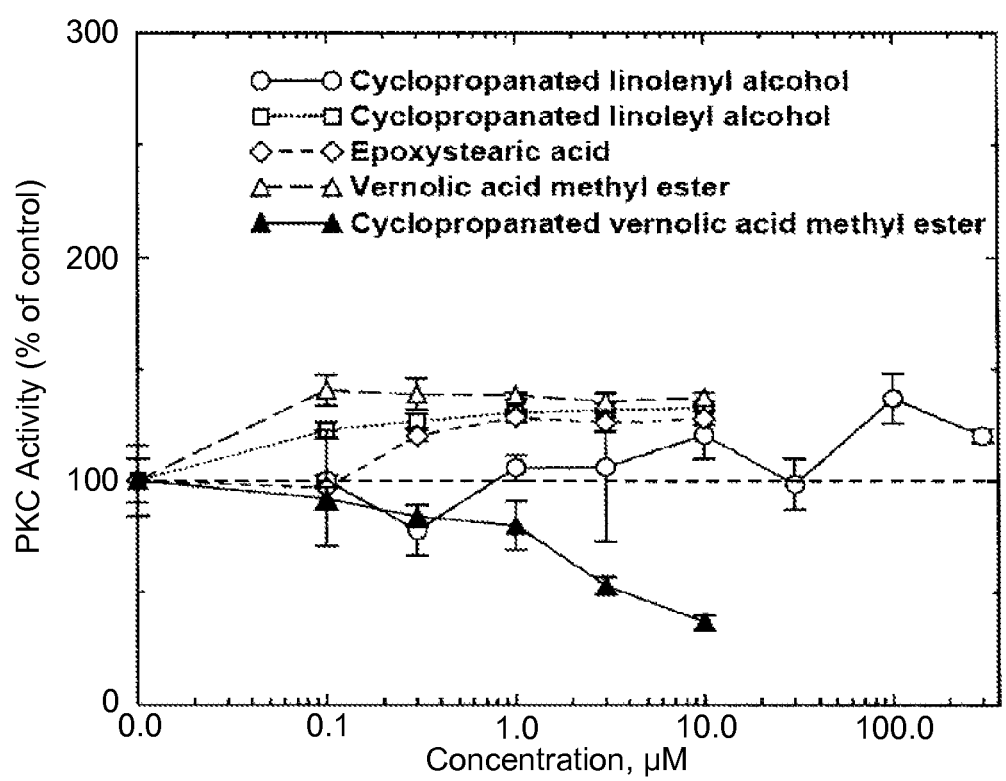
FIG. 4 shows activation of PKCε with various concentrations of other cyclopropanated and epoxidized fatty acid methyl esters:cyclopropanated linolenyl alcohol (BR-104); cyclopropanated linoleyl alcohol (BR-105); epoxystearic acid (BR-116); vernolic acid methyl ester (BR-117); and cyclopropanated vernolic acid methyl ester (BR-109).

BR-111 (DHA-CP6), BR-114 (EPA-CP5), and BR-115 (AA-CP4), which are cyclopropanated derivatives of docosahexaenoic acid, eicosapentaenoic acid, and arachidonic acid, respectively, activated purified PKCε to a similar extent (FIG. 3) The concentration needed to activate PKC was approx. 100 times lower than for BR-101 (DCP-LA), suggesting higher affinity. Cyclopropanated linolenyl and linoleyl alcohols (BR-104 and BR-105), epoxystearic acid (BR-116), and vernolic acid methyl ester (BR-117) had little or no effect on PKC (FIG. 4). Cyclopropanated vernolic acid methyl ester (BR-109) inhibited PKCε at concentrations above 1 µM (FIG. 4).

Figure 5:
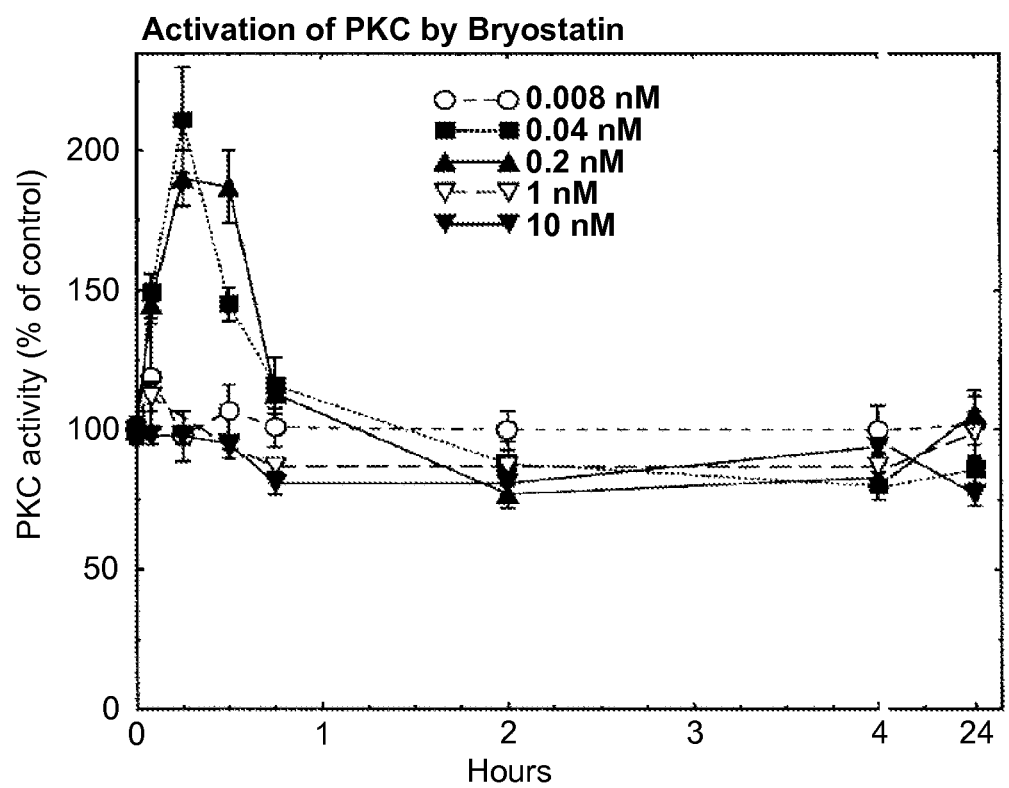
FIG. 5 shows a time course of PKC activation by various concentrations of bryostatin in H19-7/IGF-IR rat hippocampal neurons.
Figure 6:
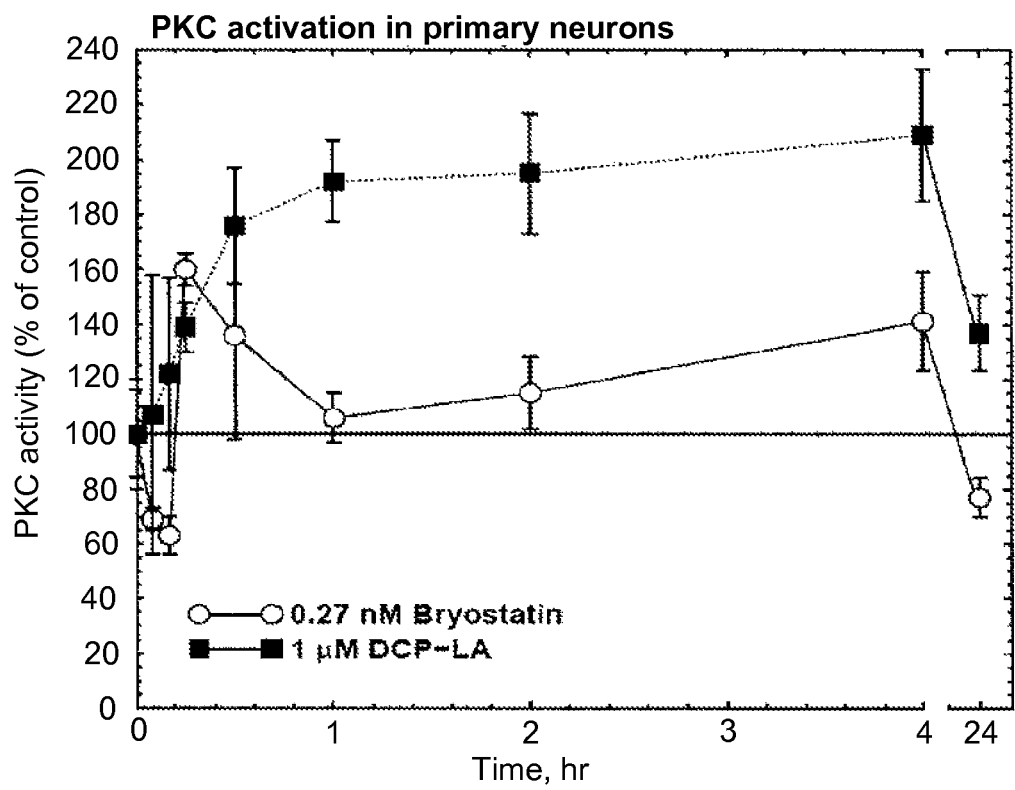
FIG. 6 shows a time course of PKC activation in rat hippocampal primary neurons by bryostatin and DCP-LA.

PKC activators that bind to the diacylglycerol binding site, including bryostatin, gnidimacrin, and phorbol esters, produce a transient activation of PKC activity, followed by a prolonged downregulation. Nelson et al., *Trends in Biochem. Sci.* 2009; 34: 136-45. This was confirmed in cultured rat hippocampal cells. Incubation of rat H19-7/IGF-IR cells with (0.04 nM and 0.2 nM) bryostatin produced a 2-fold activation that lasted 30 min, followed by a 20% downregulation that returned to baseline by 24 h (data not shown). In contrast, PKC exposed to DCP-LA remained elevated for at least four hours (FIG. 5). This sustained activation was only observed in primary neurons.

Even though bryostatin has a higher affinity for PKC than phorbol 12-myristate 13-acetate (PMA)(EC50=1.35 nM vs. 10 nM), bryostatin was much less effective than PMA at downregulating PKC. PKC activity is strongly downregulated by phorbol ester at 8 h, while PKC in bryostatin-treated cells is at or near the baseline (data not shown). This difference may explain the increases in A13 produced by PdBu reported by da Cruz e Silva et al. *J. Neurochem.* 2009: 108: 319-30. These investigators applied 1 µM PdBu to cultured COS cells for 8 h and observed an increase in Aβ. This increase was attributed to downregulation of PKC by the phorbol ester, which is consistent with these results. Downregulation could not be measured for DCP-LA and related compounds.

Example 4: Effects of PKC Activators on AB Production and Degradation

Cell culture.

Cell culture was performed as described above for Example 3.

AB Measurement and Cell Viability Assay.

Aβ was measured using an Aβ 1-42 human fluorimetric ELISA kit (Invitrogen) according to the manufacturer's instructions. Results were measured in a Biotek Synergy HT microplate reader. AlamarBlue and CyQuant NF (Invitrogen) according to the manufacturer's instructions.

Results and Discussion

Figure 7A:
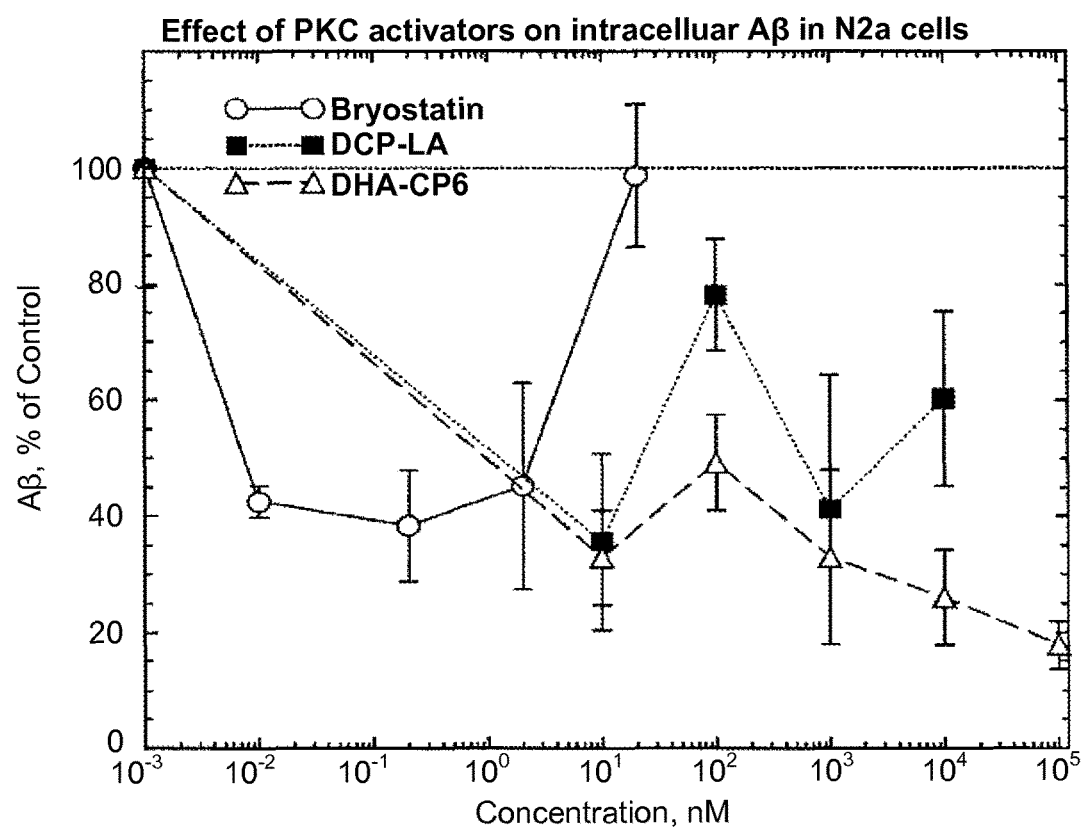
FIG. 7A depicts decreased levels of intracellular Aβ in neuro2a (N2A) cells exposed to PKC activators bryostatin, BR-101 (DCP-LA), or BR-111 (DHA-CP6).
Figure 7B:
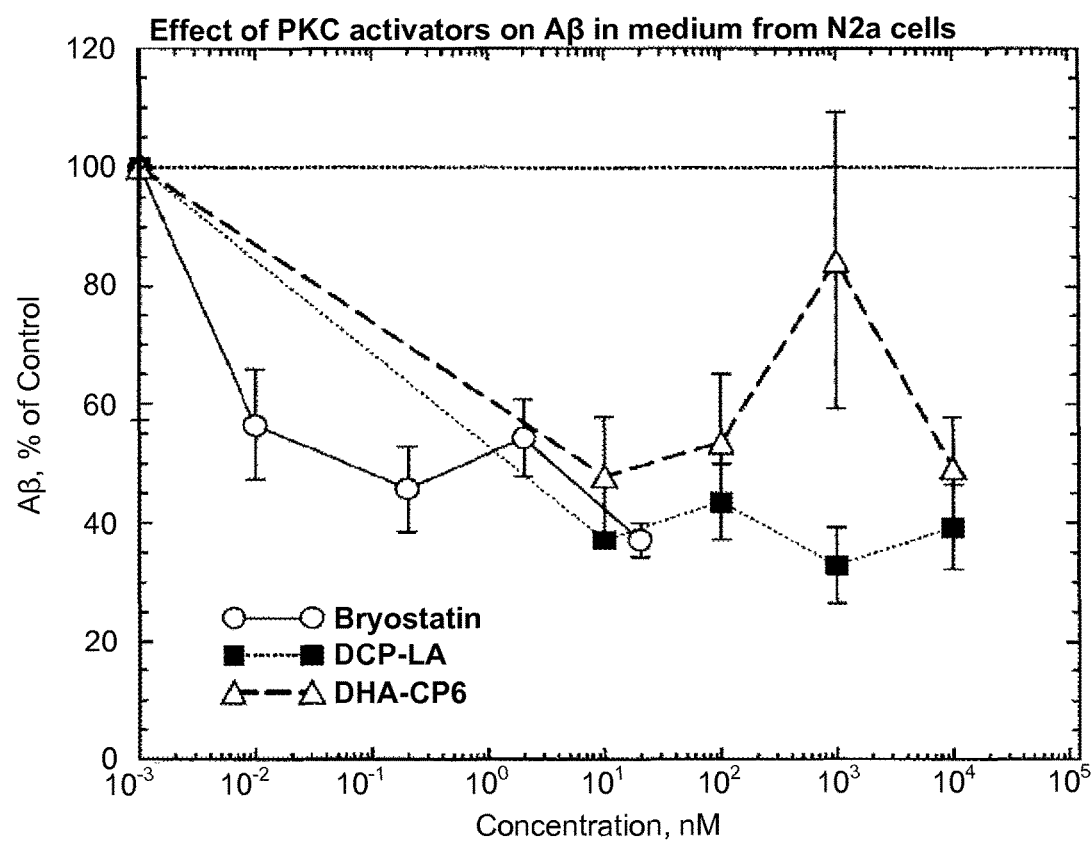
FIG. 7B depicts decreased levels of secreted Aβ in neuro2a (N2A) cells exposed to PKC activators bryostatin, BR-101 (DCP-LA), or BR-111 (DHA-CP6).

To measure the effects of PKCε activation on Aβ production, we used mouse neuro2a (N2a) neuroblastoma cells transfected with human APPSwe/PSID, which produce large quantities of Aβ. Petanceska et al., *J. Neurochem.* 1996; 74: 1878-84. Incubation of these cells for 24 h with various concentrations of PKC activators, bryostatin, BR-101 (DCP-LA) and BR-111 (DHA-CP6) markedly reduced the levels of both intracellular (FIG. 7*a*) and secreted (FIG. 7*b*) Aβ. With bryostatin, which activates PKC by binding to the diacylglycerol-binding site, the inhibition was biphasic, with concentrations of 20 nM or higher producing no net effect. This may be explained by the ability of this class of PKC activators to downregulate PKC when used at high concentrations. In contrast, BR-101 (DCP-LA) and BR-111 (DHA-CP6), which bind to PKC's phosphatidylserine site, showed monotonically increasing inhibition at concentrations up to 10 to 100 µM with no evidence of downregulation at higher concentrations.

Figure 8:
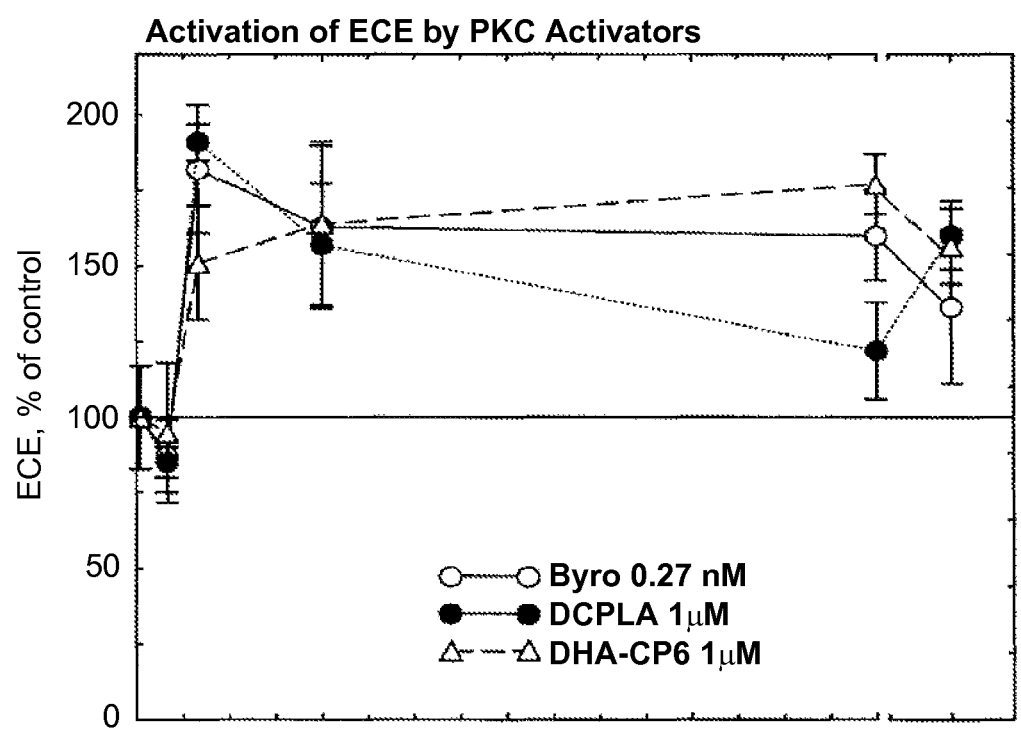
FIG. 8 shows the effect of BR-111 (DHA-CP6) (0.1 to 10 µM) on degradation of exogenously applied Aβ in SH-SY5Y neuroblastoma cells.

To determine whether the reduced levels of AP caused by PKC activators were due to inhibition of Aβ synthesis or activation of Aβ degradation, we applied BR-111 (DHA-CP6) (0.01 to 10 µM) and low concentrations (100 nM) of exogenous monomeric Aβ-42 to cultured SH-SY5Y cells. This concentration of Aβ is too low to produce measurable toxicity or cell death. Since SH-SY5Y cells produce only trace amounts of Aβ, this experiment was an effective test of the ability of PKC activators to enhance Aβ degradation. By 24 h, most of the Aβ had been taken up by the cells and the concentration of Aβ in the culture medium was undetectable. Addition of 0.01 to 10 μM DHA-CP6 to the cells reduced the cellular levels of Aβ by 45-63%, indicating that the PKCε activator increased the rate of degradation of exogenous Aβ (FIG. 8).

Figure 11A:
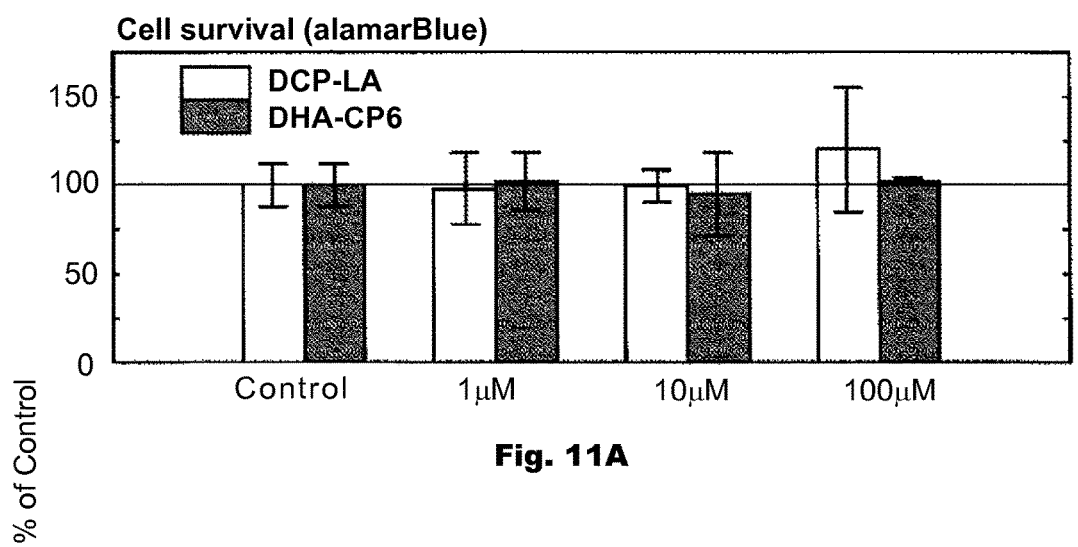
FIG. 11A depicts the effect of BR-101 (DCP-LA) and BR-111 (DHA-CP6) (1-100 µM) on cell survival of SH-SY5Y neuroblastoma cells.
Figure 11B:
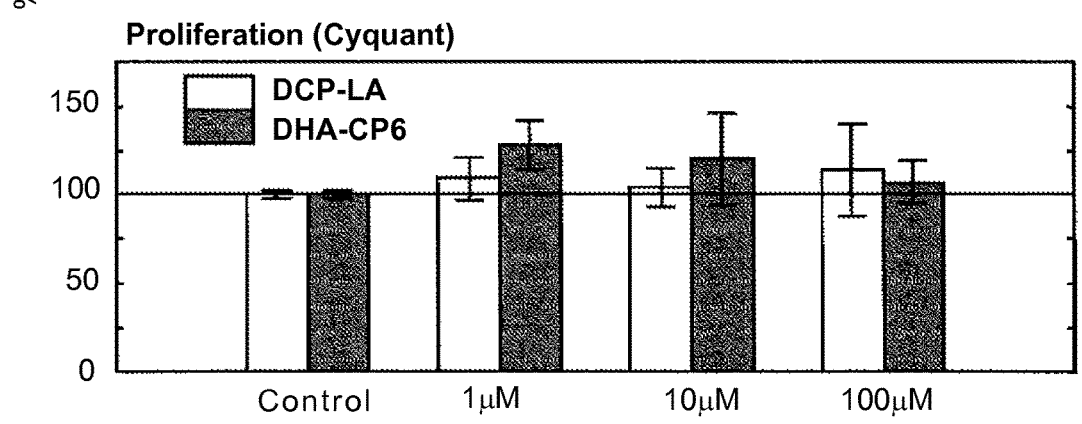
FIG. 11B depicts the effect of BR-101 (DCP-LA) and BR-111 (DHA-CP6) (1-100 µM) on cell proliferation of SH-SY5Y neuroblastoma cells.

DHA-CP6, bryostatin, and DCP-LA had no effect on cell survival or on proliferation as measured by alamar Blue and CyQuant staining (FIGS. 11a and b), indicating that the reduction in Aβ production did not result from cell proliferation or a change in cell survival.

Example 5: Effects of PKC Activators on TACE Activity

TACE Assay.

TACE was measured by incubating 5 μl cell homogenate, 3 μl buffer (50 mM Tris-HCl 7.4 plus 25 mM NaCl plus 4% glycerol), and 1 μl of 100 μM TACE substrate IV (Aβz-LAQAVRSSSR-DPa) (Calbiochem) for 20 min at 37° in 1.5-ml polypropylene centrifuge tubes (Jin et al., *Anal Biochem.* 2002; 302: 269-75). The reaction was stopped by cooling to 4° C. The samples were diluted to 1 ml and the fluorescence was rapidly measured (ex=320 nm, em=420 nm) in a Spex Fluorolog 2 spectrofluorometer.

Results and Discussion

Figure 9A:
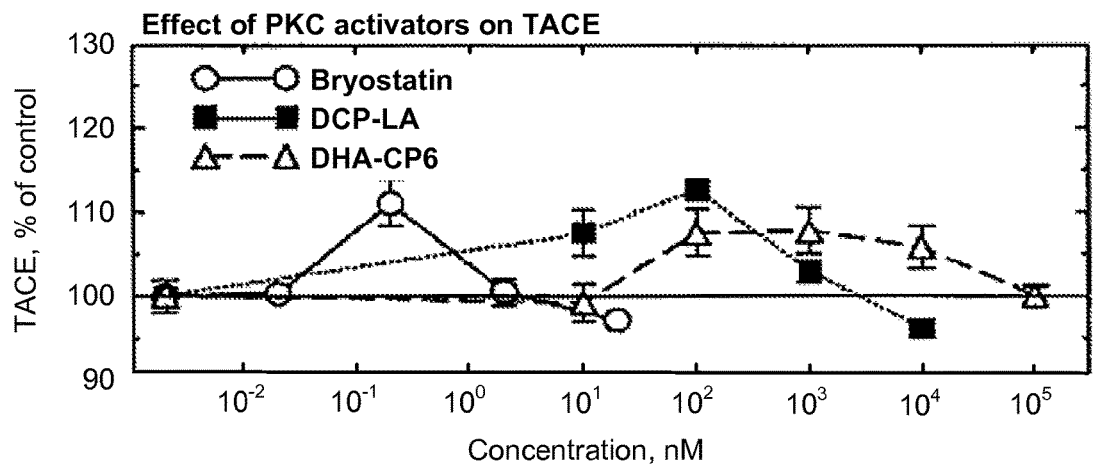
FIG. 9A depicts effects of PKC activators bryostatin, BR-101 (DCP-LA), and BR-111 (DHA-CP6) on TACE activity in N2a neuroblastoma cells transfected with human APPSwe/PSID.
Figure 9B:
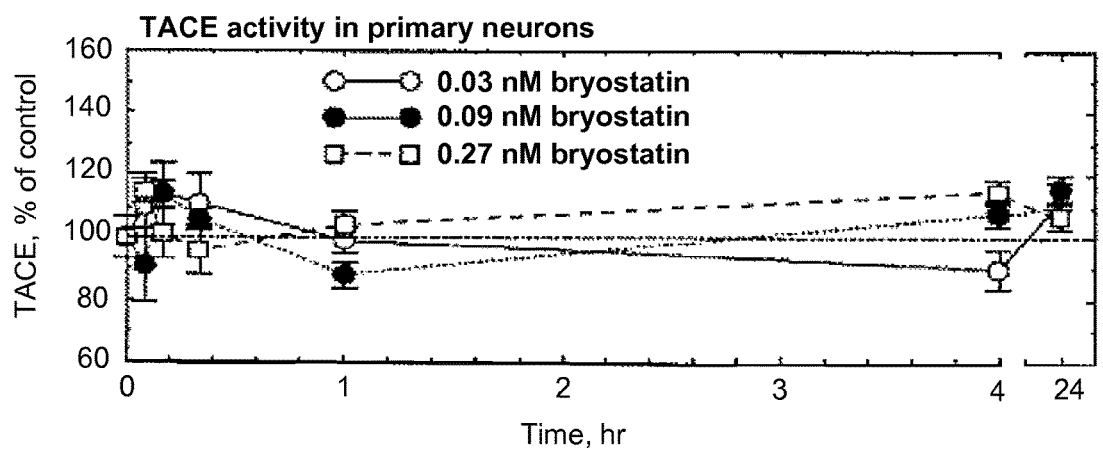
FIG. 9B depicts the effects of various concentrations of bryostatin on TACE activity in rat cortical primary neurons.
Figure 9C:
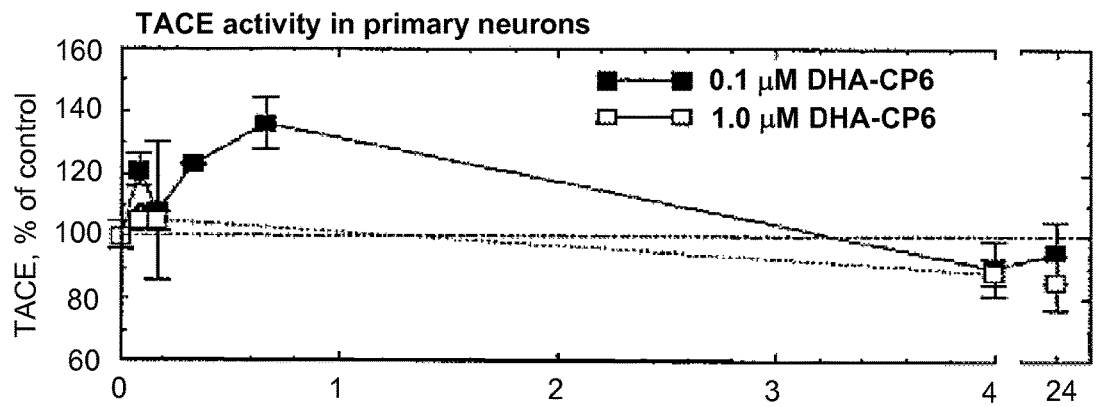
FIG. 9C depicts the effects of BR-111 (DHA-CP6) on TACE activity in rat cortical primary neurons.

Previous researchers reported that PKC activators such as phorbol 12-myristate 13-acetate produce large increases in TACE activity which correlated with increased sAPPα and decreased Aβ, suggesting that TACE and BACE1 compete for availability of APP substrate, and that PKC activators shift the competition in favor of TACE. Buxbaum et al., *J. Biol. Chem.* 1998; 273: 27765-67; Etcheberrigaray et al., *Proc. Natl. Acad. Sci. USA.* 2006: 103:8215-20. However, many of these earlier studies were carried out in fibroblasts and other non-neuronal cell types, which appear to respond differently to PKC activators than neurons. For example, Etcheberrigaray et al. found that activation of PKC in human fibroblasts by 10 pM to 100 pM bryostatin increased the initial rate of α-secretase activity by 16-fold and 132-fold, respectively (Etcheberrigaray et al., *Proc. Nail. Acad. Sci. USA.* 2006). However, in human SH-SY5Y neuroblastoma cells, N2a mouse neuroblastoma cells (FIG. 9a), and primary neurons from rat hippocampus (FIGS. 9b, c), PKC activators bryostatin, BR-101 (DCP-LA) and/or BR-111 (DHA-CP6) only produced small increases in TACE activity. This suggests that any reduction of Aβ levels in neurons by PKC activators must be caused by some other mechanism besides activation of TACE.

Example 6: Effects of PKC Activators on Endothelin-Converting Enzyme Activity

ECE Assay.

SH-S757 neuroblastoma cells were incubated with bryostatin (0.27 nM), BR-101 (DCP-LA) (1 μM), and BR-111 (DHA-CP6) (1 μM). Endothelin-converting enzyme (ECE) was measured fluorimetrically using the method of Johnson and Ahn, *Anal. Biochem.* 2000; 286: 112-118. A sample of cell homogenate (20 μl) was incubated in 50 mM MES-KOH, pH 6.0, 0.01% C12E10 (polyoxyethylene-10-lauryl ether), and 15 μM McaBK2 (7-Methoxycoumarin-4-acetyl [Ala7-(2,4-Dinitrophenyl)Lys9]-bradykinin trifluoroacetate salt) (Sigma-Aldrich). After 60 min at 37° C., the reaction was quenched by adding trifluoroacetic acid to 0.5%. The sample was diluted to 1.4 ml with water and the fluorescence was measured at ex=334 nm, em=398 nm.

Results and Discussion

Figure 10:
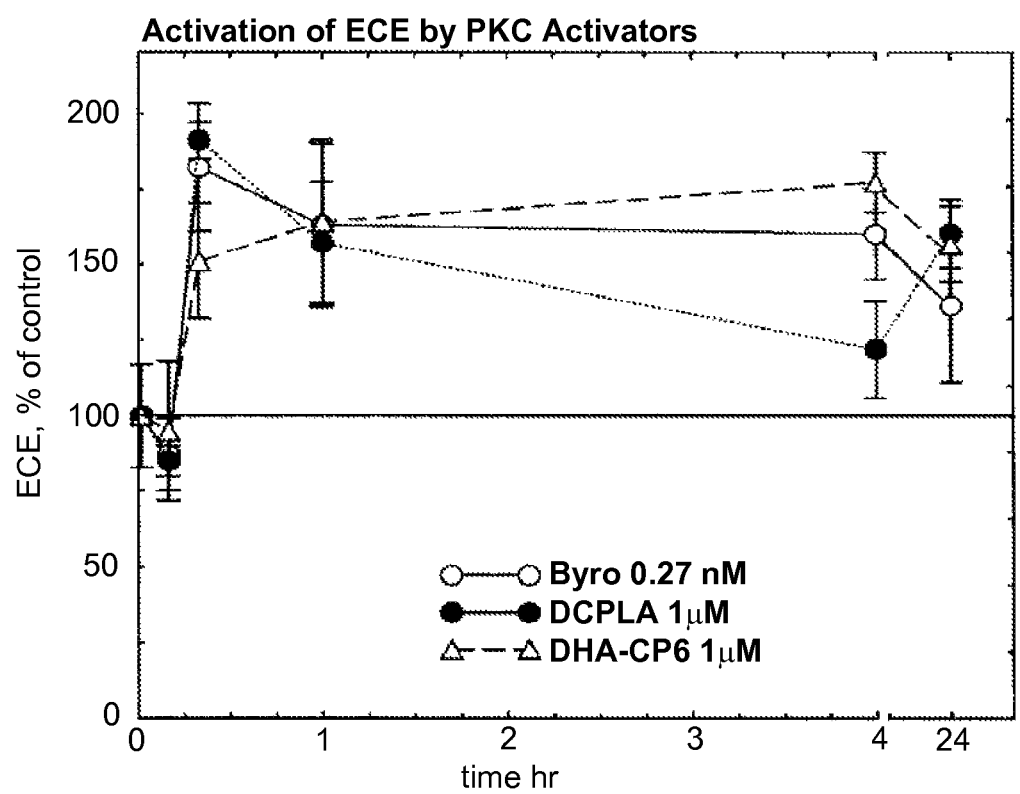
FIG. 10 shows the activation of endothelin converting enzyme (ECE) by PKC activators bryostatin (0.27 nM), BR-101 (DCP-LA) (1 µM), BR-111 (DHA-CP6) (1 µM), or ethanol in SH-SY5Y neuroblastoma cells.

Aβ can be degraded in vivo by a number of enzymes, including insulin degrading enzyme (insulysin), neprilysin, and ECE. Because PKCε overexpression has been reported to activate ECE (Choi et al., *Proc. Natl. Acad. Sci. USA.* 2006; 103: 8215-20), we examined the effect of PKC activators on ECE. Bryostatin, BR-101 (DCP-LA), and BR-111 (DHA-CP6) all produced a sustained increase in ECE activity (FIG. 10). Since ECE does not possess a diacylglycerol-binding C1 domain, this suggests that the activation by bryostatin was not due to direct activation of ECE, but must have resulted from phosphorylation of ECE or some ECE-activating intermediate by PKC. This result also suggests that indirect activation ECE by PKC activators could be a useful means of reducing the levels of Aβ in patients.

An advantage of compounds such as the PUFA derivatives of the present invention which specifically activate PKCε is that they produce less down-regulation than phorbol esters and similar 1,2-diacyl glycerol (DAG) analogues. The biphasic response of PKC to DAG-based activators means that a PKC activator may reduce Aβ levels at one time point and increase them at another. da Cruz e Silva et al., *J. Neurochem.* 2009; 108: 319-330. Careful dosing and monitoring of patients would be required to avoid effects opposite to those that are intended. Because of the relative inability of this new class of PKC activators to downregulate PKC, this problem can be avoided.

Patents, patent applications, publications, product descriptions, and protocols are cited throughout this application, the disclosures of which are incorporated herein by reference in their entireties for all purposes.

What is claimed:

1. A method for reducing neurodegeneration comprising administering to a subject in need thereof an effective amount of at least one compound chosen from a cis-monounsaturated fatty acid ester in which the double bond is replaced by a cyclopropyl group.

2. The method of claim 1, wherein the fatty acid from which the at least one compound is derived has a structure of

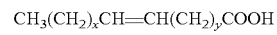

wherein x is an odd number between 3 and 11 and y is an odd number between 3 and 11.

3. The method of claim 1, wherein the fatty acid from which the at least one compound is derived is chosen from oleic acid, elaidic acid, obtusilic acid, caproleic acid, lauroleic acid, linderic acid, myristoleic acid, palmitoleic acid, vaccenic acid, gadoleic acid, erucic acid, and petroselinic acid.

* * * * *